United States Patent
Skunes et al.

(10) Patent No.: US 6,549,647 B1
(45) Date of Patent: Apr. 15, 2003

(54) INSPECTION SYSTEM WITH VIBRATION RESISTANT VIDEO CAPTURE

(75) Inventors: Timothy A. Skunes, Mahtomedi, MN (US); David Fishbaine, Minnetonka, MN (US)

(73) Assignee: CyberOptics Corporation, Golden Valley, MN (US)

( * ) Notice: Subject to any disclaimer, the term of this patent is extended or adjusted under 35 U.S.C. 154(b) by 0 days.

(21) Appl. No.: 09/522,519

(22) Filed: Mar. 10, 2000

Related U.S. Application Data
(60) Provisional application No. 60/175,049, filed on Jan. 7, 2000.

(51) Int. Cl.[7] .................................. G06K 9/00
(52) U.S. Cl. ................ 382/150; 382/147; 382/286; 348/142; 348/317
(58) Field of Search ................. 382/145, 147, 382/149, 108, 150, 286; 356/376, 512; 250/208.1; 348/297, 92, 95, 94, 129, 134, 311–317, 142, 275; 358/213.19

(56) References Cited

U.S. PATENT DOCUMENTS

| | | |
|---|---|---|
| 2,625,856 A | 1/1953 | Muller |
| 3,777,061 A | 12/1973 | Takemura ............... 178/5.4 R |
| 3,995,107 A | 11/1976 | Woywood ................ 178/7.1 |
| 4,541,010 A * | 9/1985 | Alston .................... 348/283 |
| 4,598,321 A | 7/1986 | Elabd et al. ............. 358/213 |
| 4,641,972 A | 2/1987 | Halioua et al. .......... 356/376 |
| 4,643,565 A | 2/1987 | Goto ....................... 356/24 |
| 4,677,473 A | 6/1987 | Okamoto et al. ........ 358/101 |
| 4,782,394 A * | 11/1988 | Hieda et al. ............ 358/213.19 |
| 4,835,616 A | 5/1989 | Morcom ................. 358/213.19 |
| 4,949,172 A | 8/1990 | Hunt et al. .............. 358/101 |
| 4,963,024 A | 10/1990 | Ulich ...................... 356/342 |
| 4,984,893 A | 1/1991 | Lange ..................... 356/376 |
| 5,039,868 A | 8/1991 | Kobayashi et al. ....... 250/572 |
| 5,069,548 A | 12/1991 | Boehnlein ................ 356/376 |

(List continued on next page.)

FOREIGN PATENT DOCUMENTS

| | | |
|---|---|---|
| DE | 40 11 407 A1 | 10/1991 |
| DE | 4011407 | 10/1991 |
| DE | 19 511 160 A1 | 3/1995 |
| EP | 0 453 977 A2 | 10/1991 |
| EP | 0660 078 A1 | 12/1994 |
| WO | WO 98/59490 | 6/1998 |
| WO | WO 99/12001 | 3/1999 |
| WO | WO 99/24786 | 5/1999 |
| WO | WO 0106210 A1 | 1/2001 |
| WO | WO 154058 A2 | 7/2001 |
| WO | WO 0154068 A2 | 7/2001 |
| WO | WO 02/01209 A1 | 1/2002 |
| WO | WO 02/01210 A1 | 1/2002 |

OTHER PUBLICATIONS

"Cognex and Sony Team Develops Machine–Vision Camera", *Vision Systems Design*, p. 15 (Feb. 1999).

U.S. patent application Ser. No. 09/524,133, Fishbaine et al., filed Mar. 10, 2000.

U.S. patent application Ser. No. 09/754,991, Kranz et al., filed Jan. 5, 2001.

(List continued on next page.)

*Primary Examiner*—Bhavesh Mehta
*Assistant Examiner*—Sheela Chawan
(74) *Attorney, Agent, or Firm*—Westman, Champlin & Kelly, P.A.

(57) ABSTRACT

Methods and an apparatus are disclosed for providing enhanced vibration immunity in a solder paste inspection system, although they are usable in any number of industries that require rapid acquisition of several images. The method includes capturing at least three images on a frame transfer CCD array before any data is sequentially read from the array. The present method is extendable to a larger number of images. Additionally, the masked memory area can be larger than the image area of the frame transfer CCD array.

16 Claims, 23 Drawing Sheets

U.S. PATENT DOCUMENTS

| | | | |
|---|---|---|---|
| 5,091,963 A | | 2/1992 | Litt et al. ...................... 382/8 |
| 5,103,105 A | | 4/1992 | Ikegaya et al. ............. 250/561 |
| 5,135,308 A | | 8/1992 | Kuchel ....................... 356/376 |
| 5,278,634 A | | 1/1994 | Skunes et al. ............. 356/400 |
| 5,298,734 A | * | 3/1994 | Kokubo ................... 250/208.1 |
| 5,307,152 A | | 4/1994 | Boehnlein et al. .......... 356/376 |
| 5,406,372 A | | 4/1995 | Vodanovic et al. ......... 356/394 |
| 5,424,552 A | | 6/1995 | Tsuji et al. ................. 250/548 |
| 5,450,204 A | | 9/1995 | Shigeyama et al. ......... 356/378 |
| 5,450,228 A | | 9/1995 | Boardman et al. .......... 359/209 |
| 5,455,870 A | | 10/1995 | Sepai et al. ................. 382/147 |
| 5,546,127 A | * | 8/1996 | Yamashita et al. .......... 348/297 |
| 5,636,025 A | | 6/1997 | Bieman et al. ............. 356/374 |
| 5,646,733 A | | 7/1997 | Bieman ....................... 356/376 |
| 5,668,665 A | | 9/1997 | Choate ....................... 359/663 |
| 5,684,530 A | | 11/1997 | White ........................ 348/131 |
| 5,686,994 A | | 11/1997 | Tokura ....................... 356/394 |
| 5,691,784 A | | 11/1997 | Häusler et al. ................. 349/1 |
| 5,708,532 A | | 1/1998 | Wartmann ................... 359/663 |
| 5,761,337 A | | 6/1998 | Nishimura et al. ......... 382/150 |
| 5,774,221 A | | 6/1998 | Guerra ....................... 356/376 |
| 5,815,275 A | | 9/1998 | Svetkoff et al. ............ 356/376 |
| 5,867,604 A | | 2/1999 | Ben-Levy et al. .......... 382/254 |
| 5,912,984 A | | 6/1999 | Michael et al. ............. 382/149 |
| 5,953,448 A | | 9/1999 | Liang ......................... 382/154 |
| 5,969,819 A | | 10/1999 | Wang ......................... 356/371 |
| 5,982,927 A | * | 11/1999 | Koljonen .................... 382/168 |
| 5,991,461 A | | 11/1999 | Schmucker et al. ........ 382/284 |
| 5,999,266 A | * | 12/1999 | Takahashi et al. .......... 356/376 |
| 6,061,476 A | * | 5/2000 | Nichani ...................... 382/270 |
| 6,084,712 A | | 7/2000 | Harding ...................... 359/618 |
| 6,180,935 B1 | * | 1/2001 | Hoagland ............... 250/314 R |
| 6,232,724 B1 | | 5/2001 | Onimoto et al. ............ 315/161 |
| 6,268,923 B1 | * | 7/2001 | Michniewicz et al. ...... 356/512 |
| 6,269,197 B1 | * | 7/2001 | Wallack ....................... 382/285 |
| 6,307,210 B1 | | 10/2001 | Suzuki et al. .......... 250/559.08 |

OTHER PUBLICATIONS

Copy of International Search Report from Application No. PCT/US01/00330 with international filing date of May 1, 2001.

"Accurate Machine Vision is the 'Telecentric Advantage'", 3 pages from website.

"3–D Profilometry Based on Modulation Measurement", by Likun et al., vol. 19, No. 9, pp. 1–11 (Sep. 1999).

"High Frame Rate Cameras", *Princeton Instruments Catalog of High Performance Digital CCD Cameras*, 2 pages (Oct. 1994).

"Area Array CCD Image Sensor 1024 X 1024 Pixels with Antiblooming", CCD Products, Thomson–CSF Semiconducteurs Specifiques, pp. 267–273 (1996).

"Rank Order Morphological Hit–Miss Transform and Its Optical Implementation", by Huiquan et al., ACTA OPTICA SINICA, vol. 19, No. 9, pp. 1256–1263 (Sep. 1999).

Copy of International Search Report from Application No. PCT/US00/42760 with international filing date of Dec. 12, 2000.

* cited by examiner

INSPECTION SYSTEM WITH VIBRATION RESISTANT VIDEO CAPTURE

CROSS REFERENCE TO CO-PENDING APPLICATION

This application claims priority benefits from U.S. provisional patent application Serial No. 60/175,049, filed Jan. 7, 2000, and entitled "Improved Inspection Machine".

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to the measurement of surface contours of an object using optical measurements of light reflected from the surface of the object. More particularly, this invention relates to a method and apparatus for acquiring images used in surface profilometry for such optical measurements. The invention is particularly useful for inspecting solder paste deposited on electronic circuit boards during the circuit board fabrication process.

BACKGROUND OF THE INVENTION

Circuit boards that carry electronic integrated circuits as well as discrete electronic components are well known. A circuit board substrate is prepared with predetermined conductor paths and pads for receiving the lead of an electronic component such as integrated circuit chips, resistors or capacitors. During the circuit board fabrication process, solder paste bricks are placed onto the board substrate at appropriate positions. The solder paste is usually applied by placing a screen onto the substrate, applying solder paste through the screen openings, wiping the excess solder paste from the screen surface, and removing the screen from the substrate. The circuit board electronic components are then positioned onto the substrate, preferably with a pick and place machine, with leads of the electronic components placed on their respective, appropriate solder paste bricks. The circuit board is passed through an oven after all of the components are positioned on a substrate, to melt the solder paste thus creating an electrical as well as a mechanical connection between the components and the substrate.

The size of the solder paste bricks, and the accuracy with which they must be placed on the substrate, has become increasing smaller and tighter with the increased emphasis on miniaturization in the electronics industry. Solder paste brick heights can be as small as 200 microns in diameter and having a height of 100 microns. The height of the solder paste brick must often be measured to within 1 percent of the designed height. The center to center spacing between two adjacent solder paste bricks may be as low 300 microns. Too little solder paste in one brick can result in the failure to provide an electrical connection between the lead of an electronic component and the pad of the circuit board substrate. Too much paste in one brick can result in bridging and short-circuiting between the leads of a component.

A single circuit board can cost thousands and even tens of thousands of dollars to manufacture. Testing of a circuit board after the fabrication process is complete can detect errors in solder paste placement and component lead connection, but often the only remedy for a faulty board is scrapping of the board. It is accordingly imperative that a circuit board be inspected during the fabrication process so that improper solder paste placement can be detected prior to the placement of the electronic components onto the substrate. Such in-process solder inspection reduces the cost of failure since expensive components have not yet been placed onto the circuit board.

One important characteristic that is measured during solder paste inspection is the height of each solder brick. Once the height is known and the boundaries of the deposit are located, the volume of paste deposits can also be calculated. One way in which the heights of solder bricks have been measured is by using a technique known as phase profilometry. In some types of phase profilometry, the surface profile of an object of interest is computed by projecting at least three phases of a light pattern onto the object and capturing those images, and then computing the surface profile as a function of the three captured images. One particular method and apparatus for phase profilometry using three or more images is disclosed in U.S. Pat. No. 4,641,972 entitled "Method and Apparatus for Surface Profilometry." However, the method and apparatus of the '972 patent suffers from susceptibility to system vibration. Such susceptibility renders the system disclosed in the '972 patent unsuitable for industrial applications in high vibration environments.

Vibration immunity is very important for profilometry systems when they rely upon the surface feature (e.g. solder brick) to be essentially in a known position while sequentially exposed to each of the projected patterns. Automated electronics assembly lines often generate a relatively large amount of vibration. It is generally preferred to locate the solder paste inspection machine within the assembly line such that it inspects solder paste immediately after paste deposition and before component placement. However, the proximity of the solder paste inspection machine to other machines introduces vibrations, which can adversely affect solder paste inspection. For example, when a surface feature on the circuit board (such as a solder brick) vibrates, it appears in one place when imaged with a first projected pattern and appears in other places when imaged with successively projected light patterns, leading to errors in the resulting map of surface heights.

Therefore, it is important to the field of surface profilometry to minimize uncontrolled displacement between successively captured images. If all the required images can be acquired within approximately 1 millisecond or less, the images will be substantially immune to vibration in most industrial environments. The immunity is provided by the fact that the vibrating surface does not travel appreciably in one millisecond.

One method for electronically capturing images for optical inspection uses a frame transfer Charge Coupled Device (CCD) array. One such device is the Model THX 7887A available from Thompson-CSF Semiconducteurs Specifiques of France. A frame transfer CCD array is a photosensitive semiconductor device that includes an image area as well as a memory area thus allowing an image stored in the memory area to be read out, while another image is acquired in the image area. While these conventional arrays can be configured to permit the rapid acquisition of two images, they have been unable to do so for the three images required in advanced systems.

Thus, there is a need for an inspection system and an associated method, which can capture three or more successive images within a period of about 1 millisecond in order to provide an industrial profilometry system that is substantially immune to vibration.

SUMMARY OF THE INVENTION

Methods and an apparatus are disclosed for providing enhanced vibration immunity in a solder paste inspection system, although they are usable in any number of industries that require rapid acquisition of several images. The method includes capturing at least three images on a frame transfer CCD array before any data is sequentially read from the array. The present method is extendable to a larger number of images. Additionally, the masked memory area can be larger than the image area of the frame transfer CCD array.

DETAILED DESCRIPTION

Figure 1:
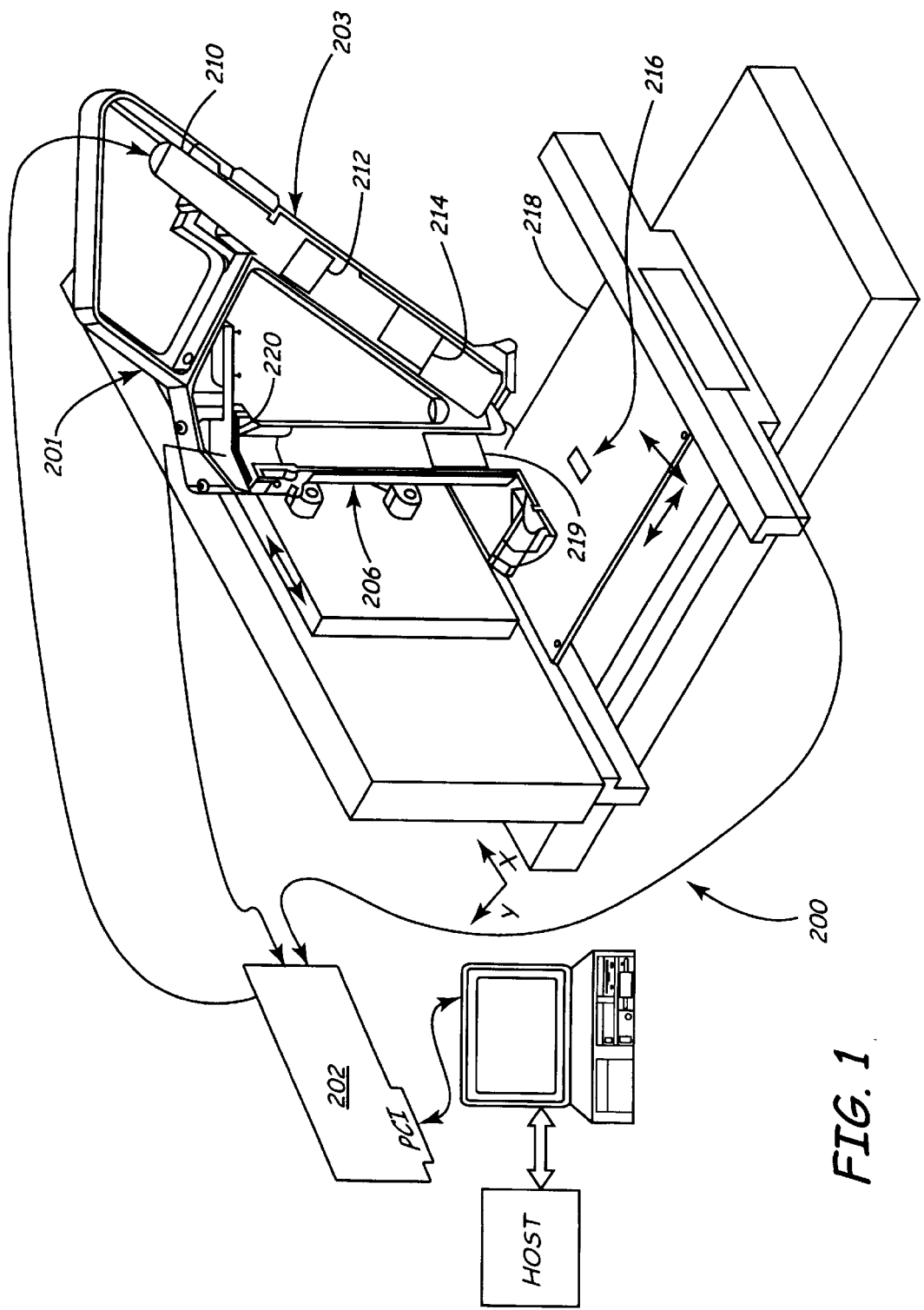
FIG. 1 is a diagrammatic view of a novel solder paste inspection system.

FIG. 1 is a diagrammatic view of solder paste inspection system 200. System 200 is merely one exemplary paste inspection system with which embodiments of the present invention are useful. Those skilled in the art will recognize that embodiments of the present invention are useful with other types of inspection systems, and such embodiments are expressly contemplated.

System 200 includes processor 202 and sensor 201. Sensor 201 includes projector 203, and imaging system 206. Projector 203 includes illuminator 210, grating 212, and optics 214. Illuminator 210 can be any light source capable of providing short duration light pulses, such as a pulsed laser or strobe lamp. Grating 212 imparts a pattern on light passing therethrough, and optics 214 focus the patterned light upon feature 216 on circuit board 218. Imaging system 206 includes optics 219, which focus the image of feature 216 upon frame transfer CCD array 220. Processor 202 is coupled to projector 203 such that processor 202 triggers projector 203 to illuminate feature 206 on circuit board 208. Sensor 201 is adapted to project patterned images of different phases upon feature 216.

Sensor 201 is adapted to acquire images of feature 216 while exposed to the multiple patterns, such that each image corresponds to a different phase. CCD array 220 provides data representative of the acquired images to processor 202 which computes a height map of feature 216 based upon the acquired images. The height map is useful for a number of inspection criteria such as volume calculation and bridge detection.

Figure 2:
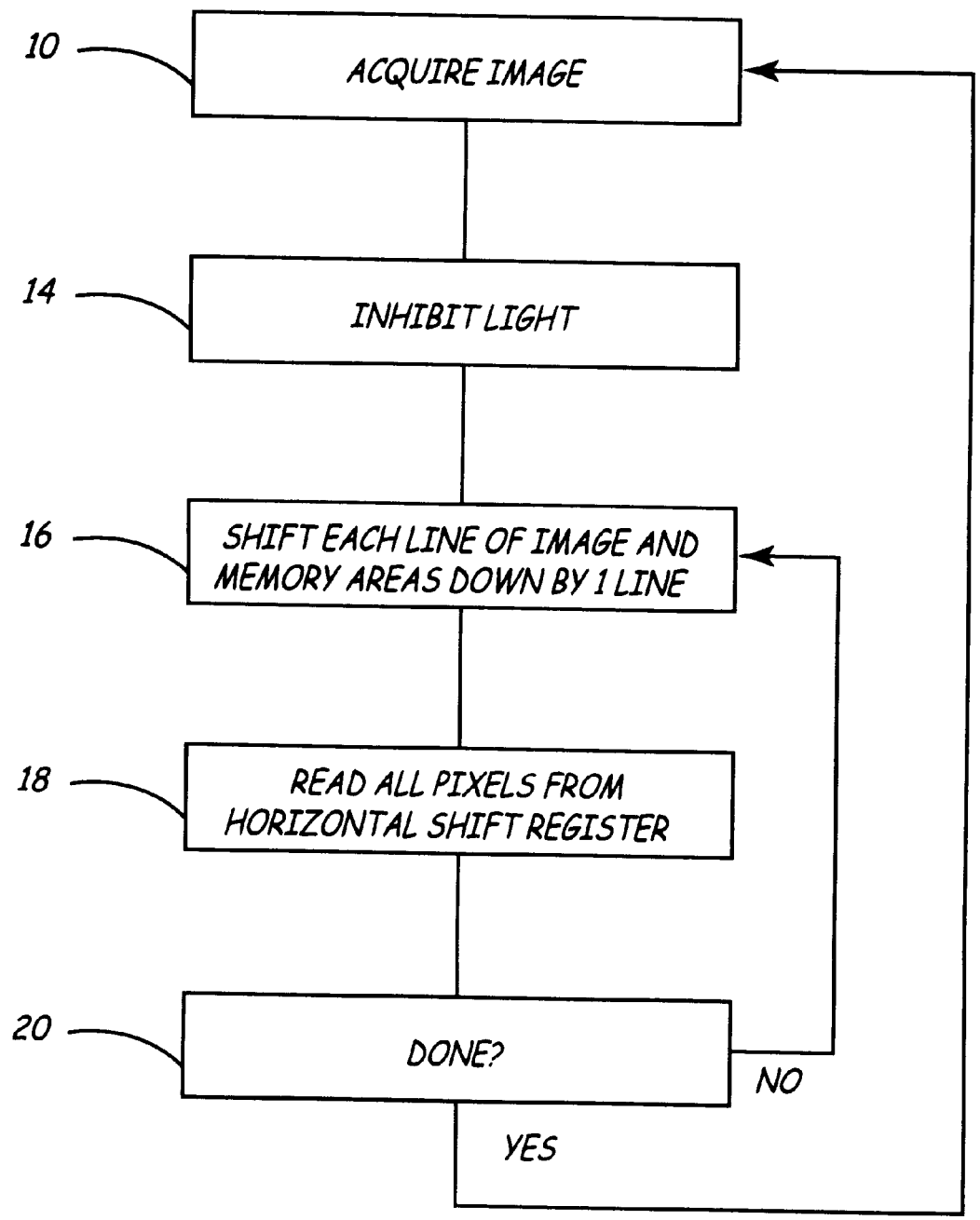
FIG. 2 is block diagram of a method of acquiring and reading out an image from a frame transfer CCD array.

FIG. 2 is a block diagram illustrating one method using a frame transfer CCD. The frame transfer CCD array operates both as an image sensor and as an analog storage device. An image is exposed on image area 30 (shown in FIG. 3), and charge created in that exposure is electronically shifted vertically into masked memory area 34 at about 0.8 microseconds per row. Once all the charge from those pixels which make up the first image area are shifted into the memory area, the next exposure may begin. The method begins at block 10 where a photosensitive area 30 of CCD array 32 (shown in FIG. 3) is exposed to light for a period of time. As used herein, light is intended to mean electromagnetic energy from ultraviolet to infrared. The photosensitive two-dimensional array of pixels within CCD array 32 generates charge packets based upon light exposure. CCD array 32 also includes memory area 34, which is masked from the light. The image area is preferably 1024×1024 pixels and the memory area is preferably 1024×1024 pixels. At block 14, the light is turned off or a mechanical shutter is engaged to inhibit additional light from striking image area 30 of the CCD array 32. At block 16, clock signals $\phi_I$ and $\phi_M$ are provided to the image area as well as the memory area such that each line of stored image in the image area and the memory area is shifted down one line. In the process of shifting image area 30 down by one line at a time, the top line of area 30 is reset or filled with "black level" pixels. Additionally, the bottom line of CCD memory area 34 is transferred into horizontal shift register 36. At block 18, the contents of horizontal shift register 36 are read out serially to video amplifier 38. Block 20 checks to see if all lines of an image have been stored in the memory area, and that the contents of the memory area have been read out. If not, control passes to block 16. However, if all lines of an image are stored in the memory area, then control passes back to block 10 where the image area is once again exposed.

Typical horizontal shift register clock, $\phi_H$, periods are about 50 nanoseconds for commercially available devices. Sequentially clocking out 1,024 pixels representing one image out of horizontal shift register 36 thus takes about 51 microseconds. Additionally, typical memory area clock, $\phi_M$, and image area clock, $\phi_I$, are about 800 nanoseconds. Therefore, once the image integration period is over, it takes about 53 milliseconds to clock out video data from the memory area and shift the image area to the memory area. Fifty-three milliseconds for one image is significantly longer than the goal of one millisecond for three or more images and thus renders such prior art methods for data acquisition susceptible to system vibration.

Figure 3:
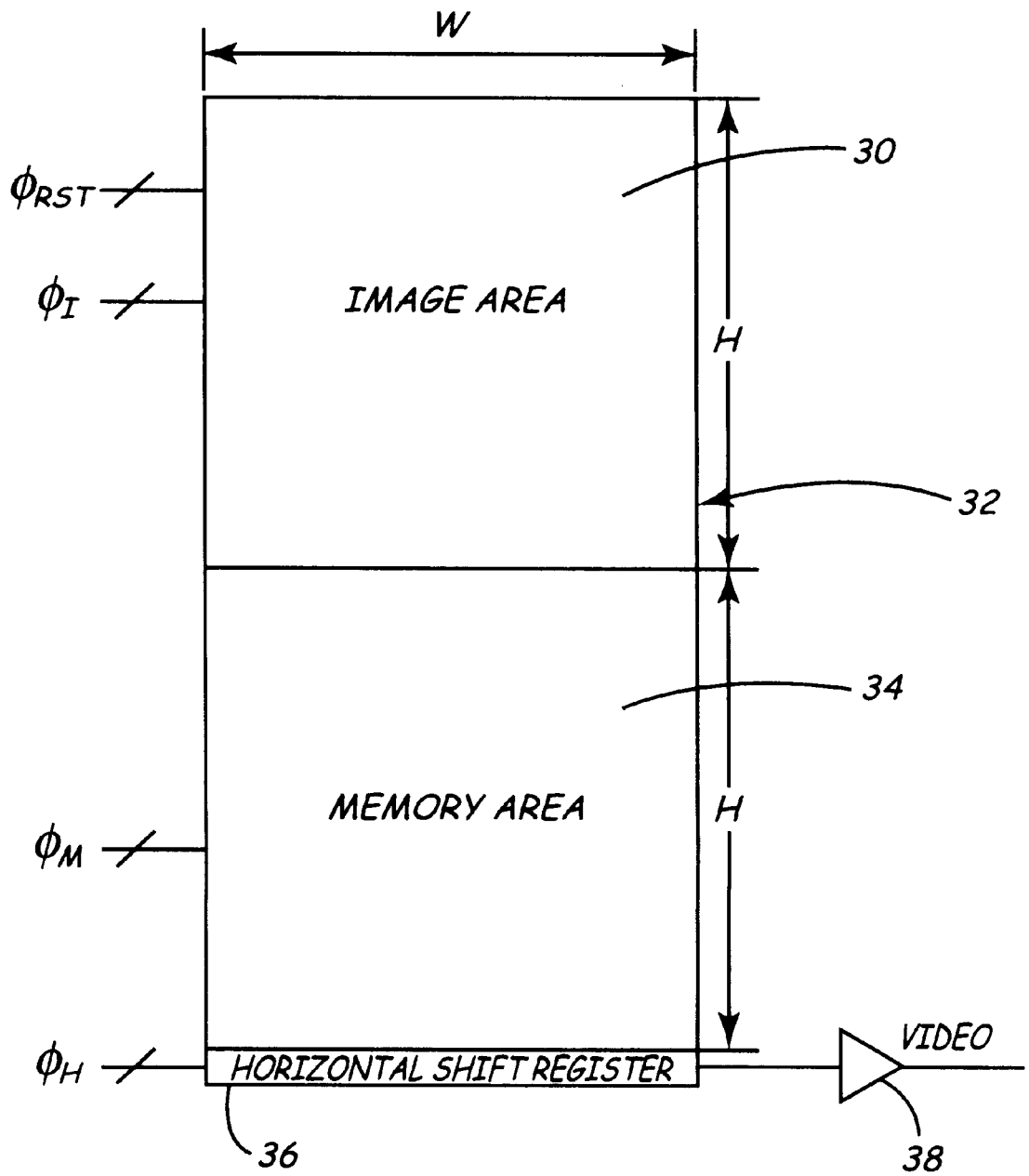
FIG. 3 is a diagrammatic view of a conventional frame transfer CCD array.
Figure 4:
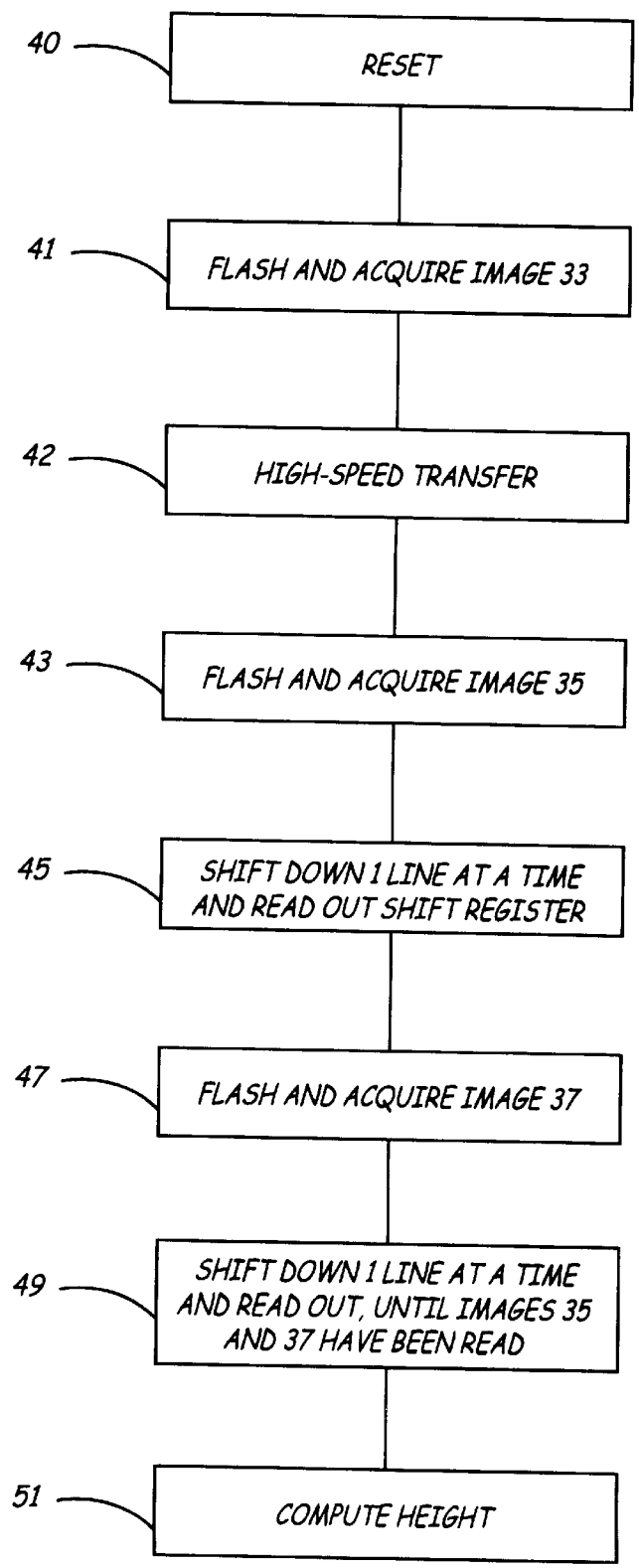
FIG. 4 is a block diagram of a method of acquiring three fringe pattern images using the array of FIG. 3.
Figure 5:
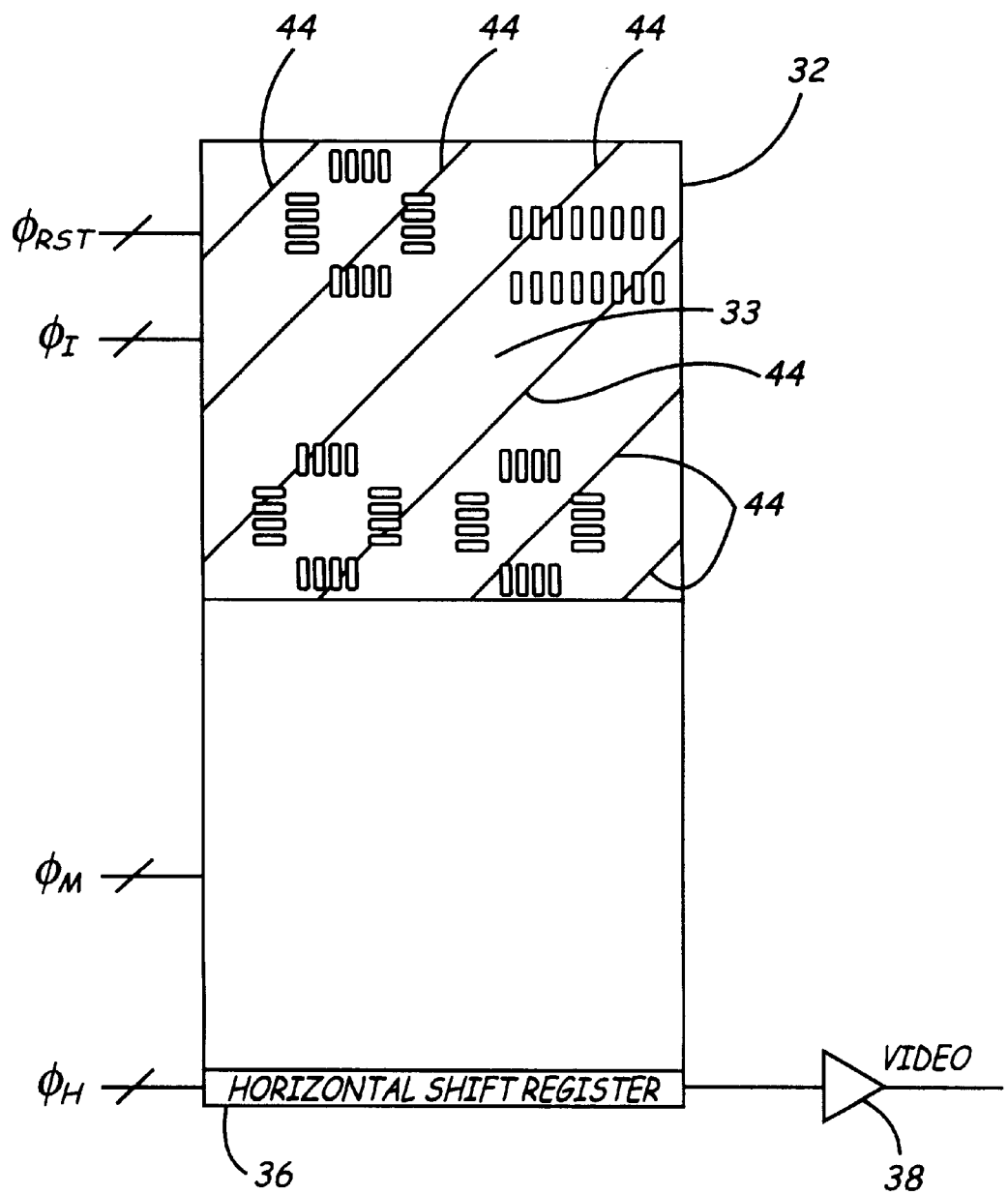
FIGS. 5–9 illustrate frame transfer CCD array status at various stages during execution of the method shown in FIG. 4.
Figure 6:
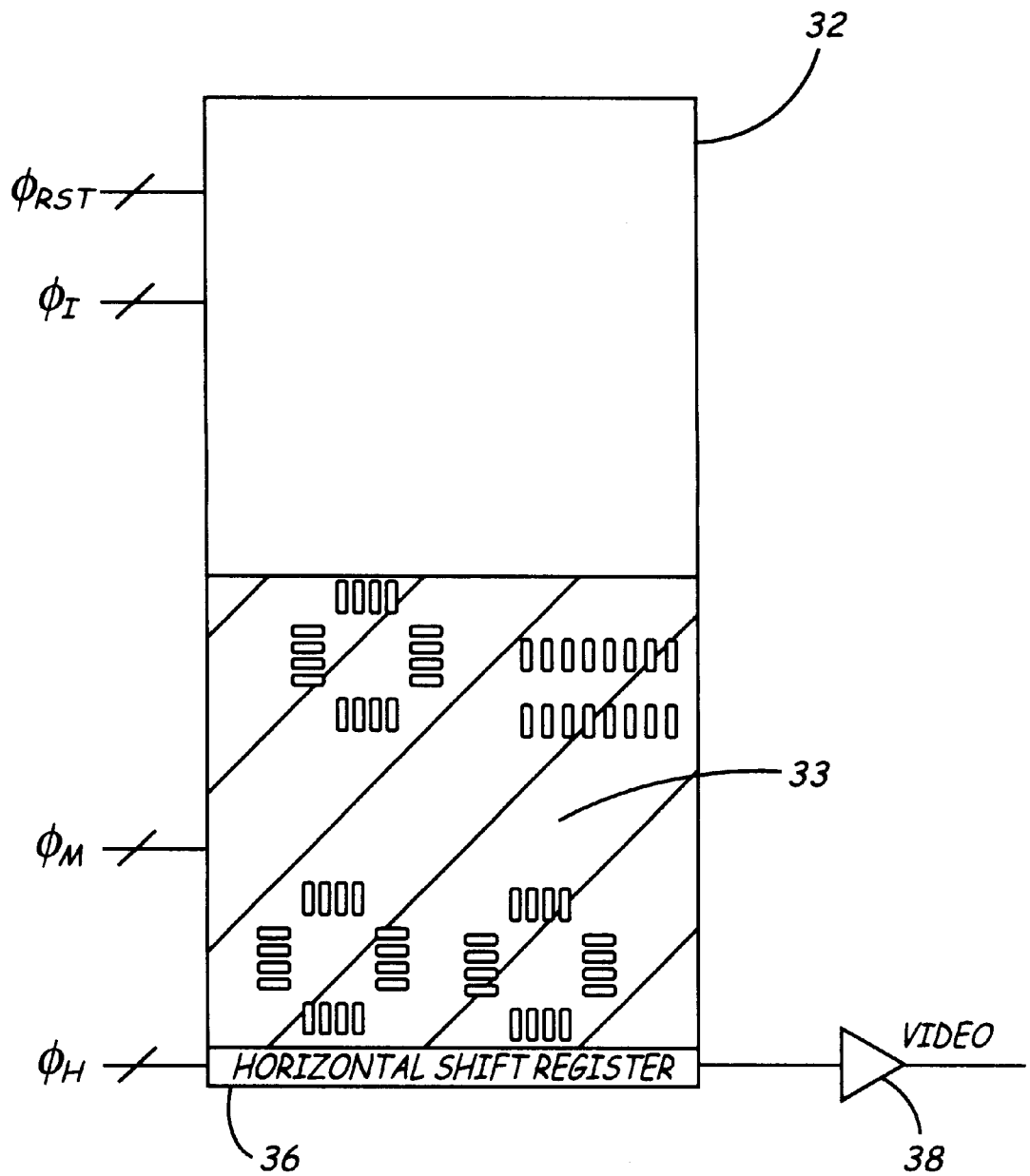

FIG. 4 is a block diagram of a method of capturing three sets of fringe pattern images with a conventional frame transfer CCD device. The method begins at block 40 where the image area of the CCD array is reset using $\phi_{RST}$ (shown in FIG. 5). This reset causes undesirable charge accumulated during system rest to be discharged. At block 41, an illuminator is flashed to expose image area 30 to the first fringe pattern image. Any other method of illuminating the surface of interest can be used. For example, a mechanical shutter over the CCD array can also expose the array to illumination, with a constant light source. This exposed image is illustrated in FIG. 5 at reference numeral 33 for an exemplary solder paste image. The diagonal lines 44 represent the peaks of the sinusoidal fringes which are distorted where they cross the solder paste deposit. Preferably, the illumination duration is about 20 microseconds. Referring to FIG. 4, the method continues at block 42 where a high speed image transfer is accomplished by clocking $\phi_I$ and $\phi_M$ together H times to transfer charge packets from image area 30 to memory area 34. H is shown in FIG. 3, and is preferably 1024. This high speed transfer takes approximately 800 microseconds, and is limited by the maximum clock speed of the CCD array in use. The results of block 42 are shown in FIG. 6 where the acquired image has now been transferred into masked memory area 34 of the CCD array 32. Memory area 34 now holds the first fringe pattern image and image area 30 has been reset.

Figure 7:
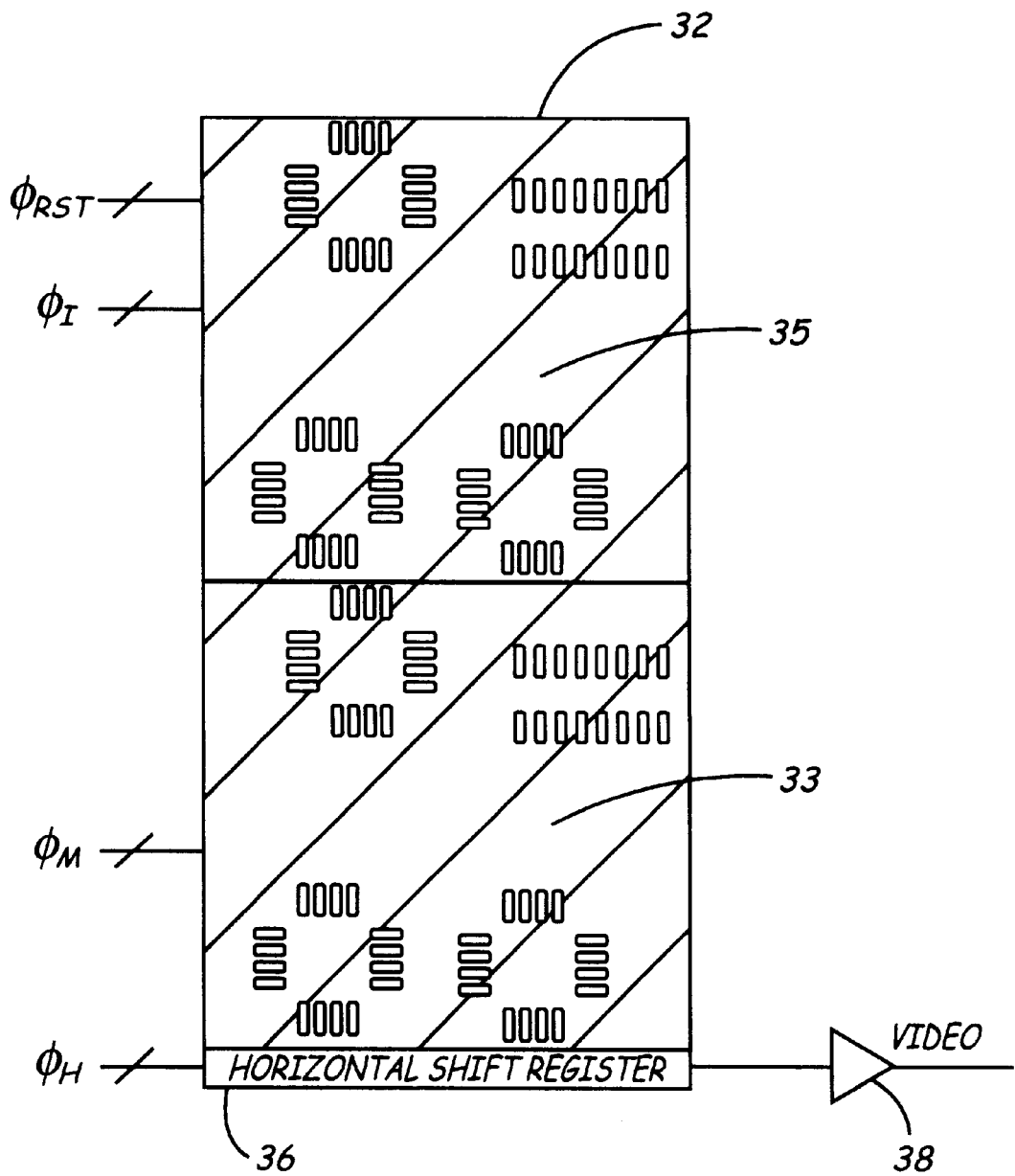
Figure 8:
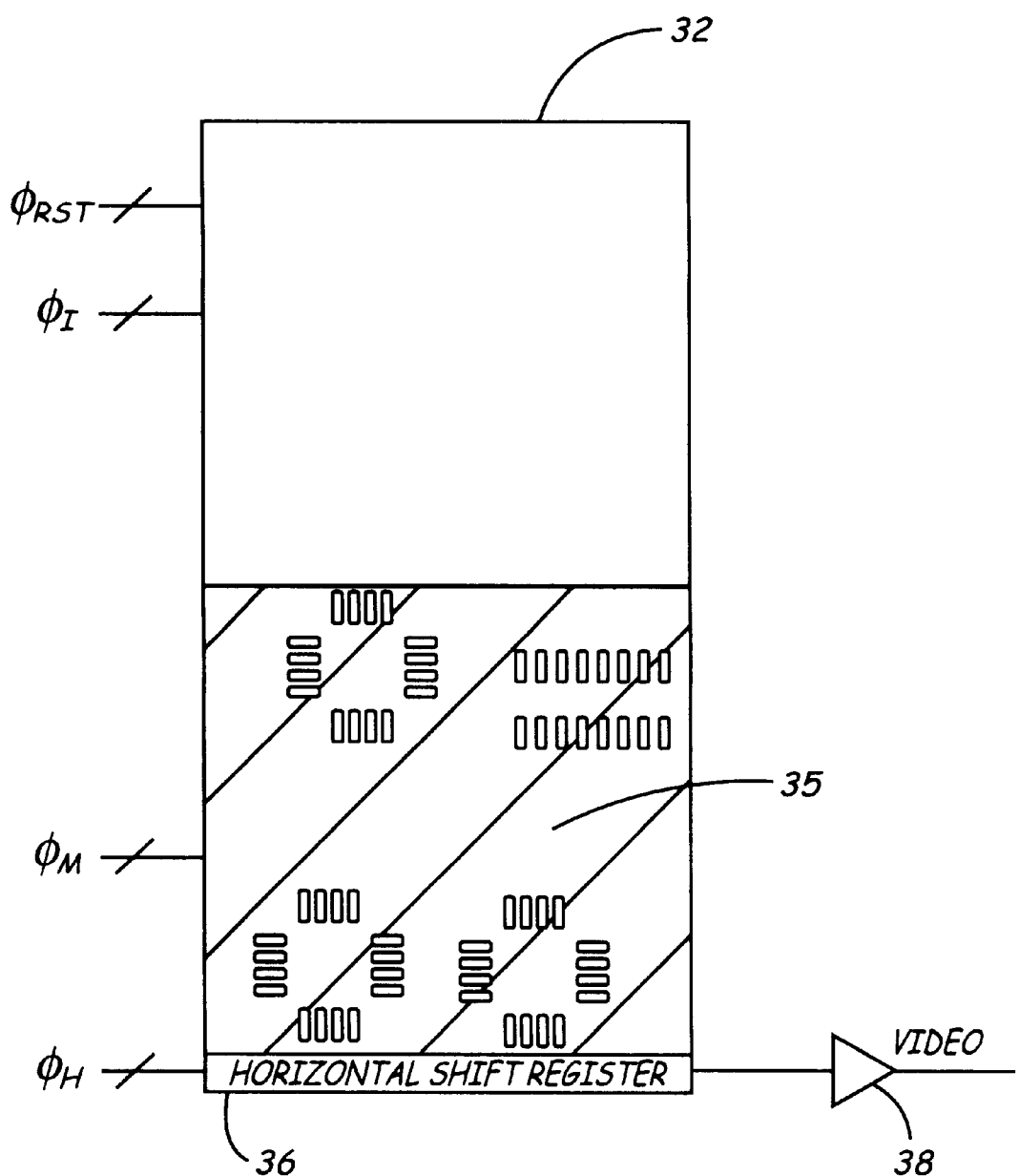
Figure 9:
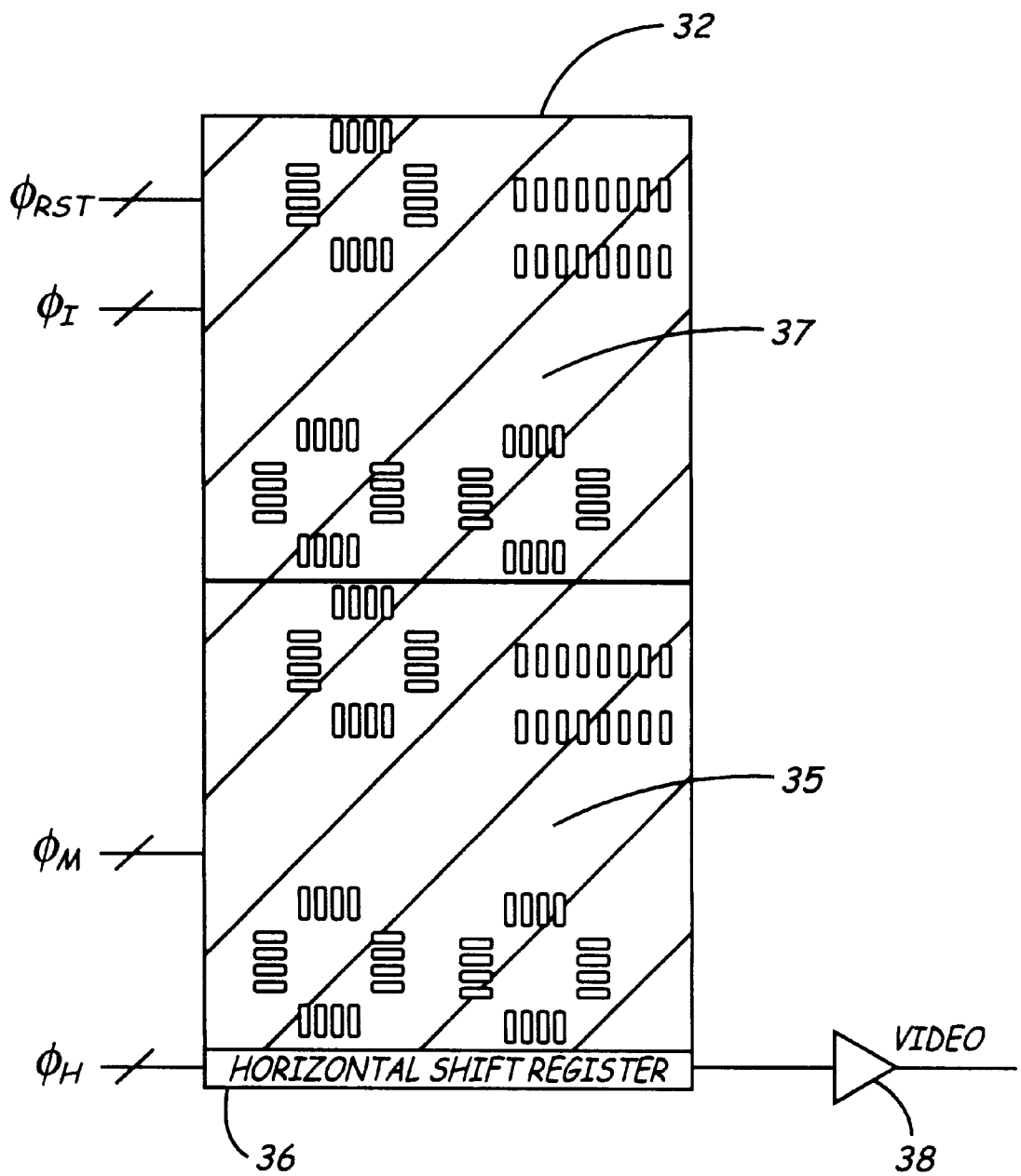

Referring back to FIG. 4, at block 43 the illuminator is pulsed again to expose image area 30 to the second fringe pattern image. Thus, a second fringe pattern image is now held by image area 30 and the first fringe pattern image is still held in masked memory area 34. Block 43 preferably takes approximately 20 microseconds and results in images being stored as shown in FIG. 7 with the second image labeled as reference numeral 35. Note that fringes in image 35 are shifted with respect to the fringes in image 33. The phase shift is preferably 120 degrees, but other shifts can be used. Referring back to FIG. 4, the method continues at block 45 with the previously described process of shifting charge packets out of the horizontal shift register 36 and then shifting the image and memory areas down a line at a time. Block 45 continues until the first fringe pattern image has been read out and the second fringe pattern image is stored in memory area 34. This takes about 53 milliseconds as mentioned above with respect FIG. 2. FIG. 8 shows the results of completion of block 45. Once block 45 has completed, the illuminator is flashed again, at block 47, and a third image is acquired in image area 30 of CCD array 32. This final operation takes approximately 20 microseconds and the results of block 52 are illustrated in FIG. 9 with the third image labeled as reference numeral 37. Note, fringes in image 37 are shifted 120 degrees with respect to that of image 35. At block 49, the entire contents of CCD array 32 are iteratively shifted down and read from shift register 36 until both of images 35 and 37 have been read. At block 51, the three images 33, 35, 37 are used to compute a height map of the imaged features. Representative times are shown below in Table 1.

TABLE 1

| Function | Time |
| --- | --- |
| Flash and Acquire #33 | 20 microseconds |
| High Speed Transfer | 800 microseconds |
| Flash and Acquire #35 | 20 microseconds |
| Shift 1 line at a time and read out, until all of image #1 has been read | 53 milliseconds |
| Flash and Acquire #37 | 20 microseconds |
| Total | About 54 milliseconds |

To summarize the execution of the method illustrated in FIG. 4, all three sets of fringe pattern images were captured in approximately 54 milliseconds. It takes about another 106 milliseconds to read out the second and third fringe pattern images. However, one important parameter in determining the system's immunity to vibration is the capture time for all three sets of fringe pattern images. Fifty four (54) milliseconds, of course, is too slow to meet the goal of capturing the images in approximately 1 millisecond or less, as set forth above.

A review of the various times required for execution of the method shown in FIG. 4 revealed that the high speed image transfer from image area 30 to memory area 34 is approximately 60 times faster than sequentially reading all of the charge packets for one image out of horizontal shift register 36. Thus, dramatic reduction in the capture time for all three fringe pattern images is realized by modifying conventional frame transfer CCD array architecture to that shown in FIG. 10.

Figure 10:
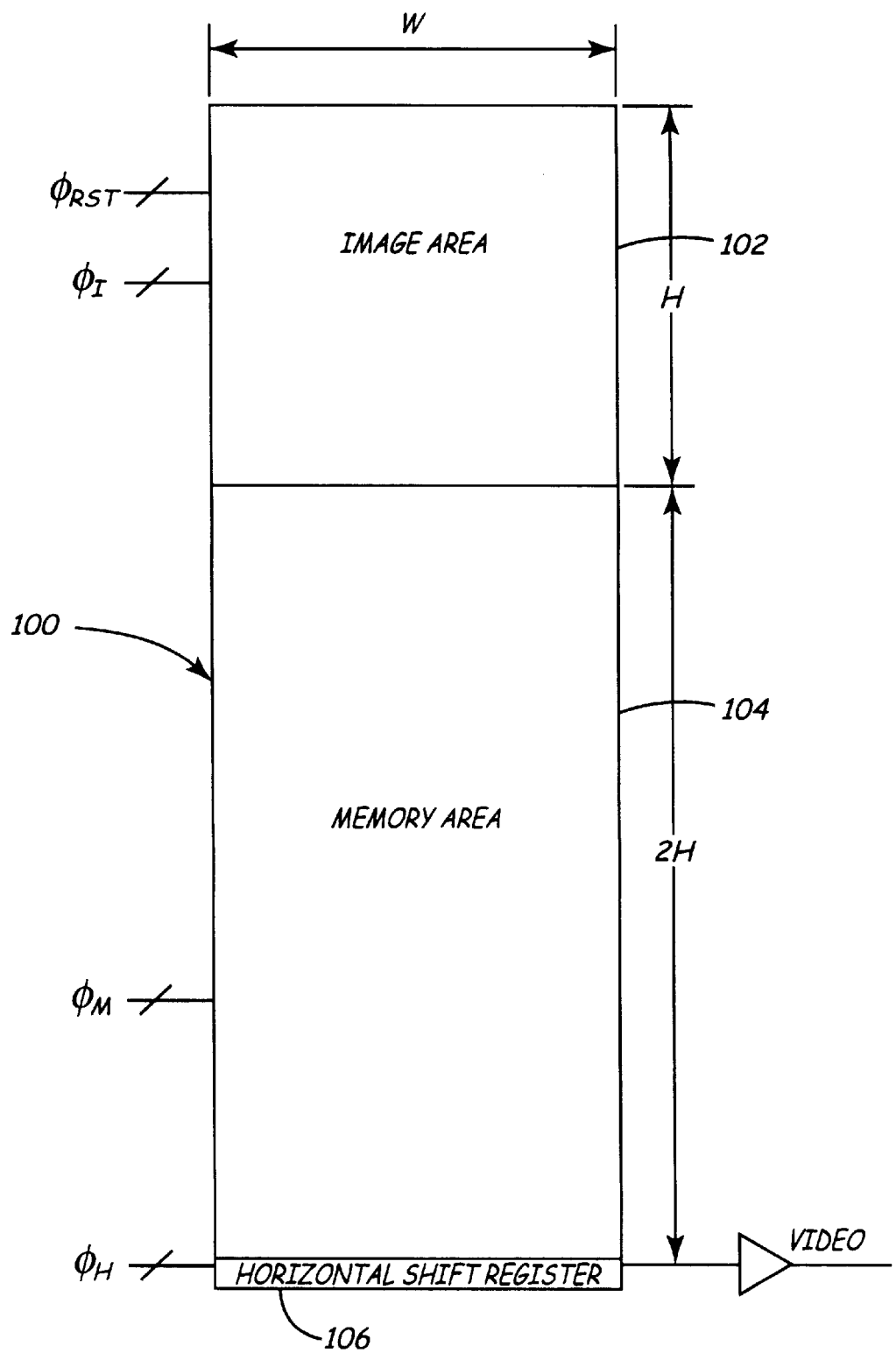
FIG. 10 is a diagrammatic view of a frame transfer CCD array.

FIG. 10 is a diagrammatic view of CCD frame transfer array 100 in accordance with one embodiment of the present invention. CCD array 100 includes image area 102, memory area 104, and horizontal shift register 106. Note that image area 102 and memory area 104 have identical widths, but memory area 104 has a height (H) that is twice as large as area 102. Preferably, H and W are each 1024. Memory area 104 is now capable of storing a plurality of complete acquired images.

Figure 11:
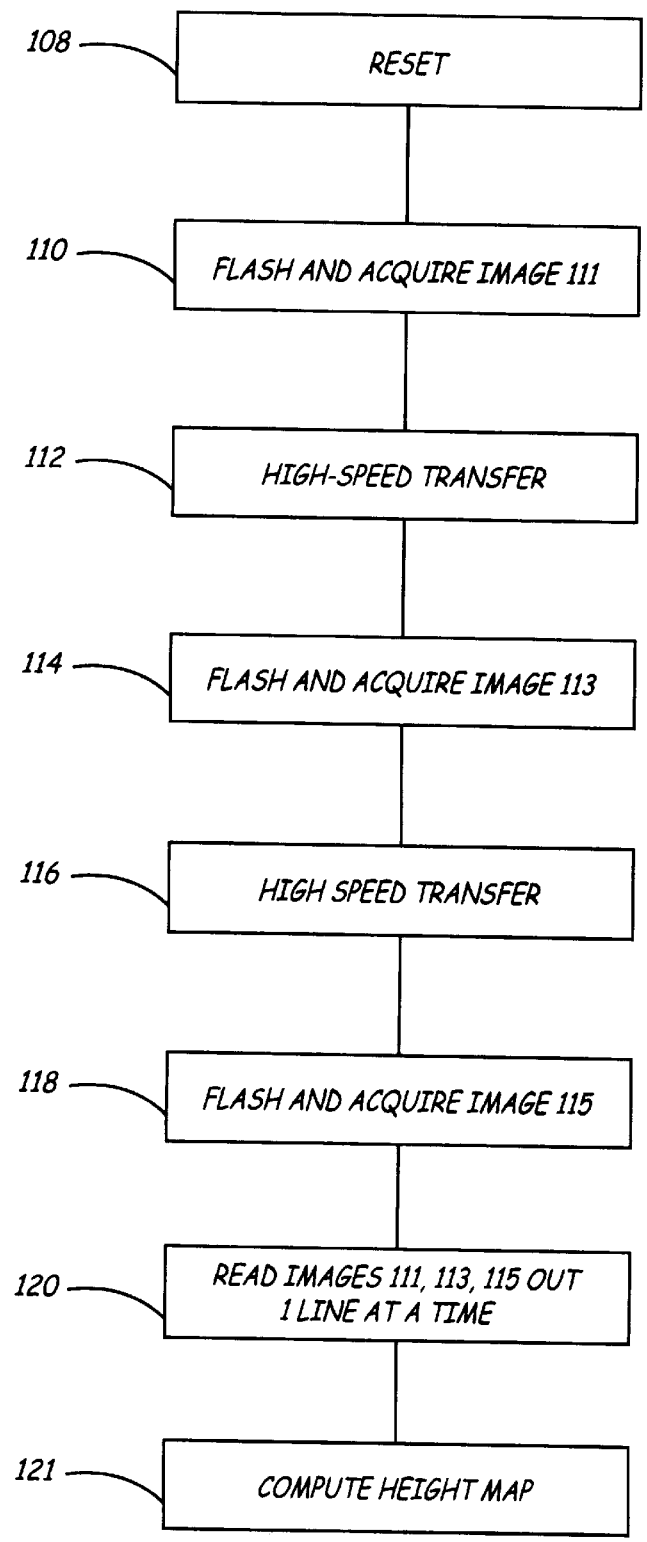
FIG. 11 is a block diagram of a method of acquiring three fringe pattern images.
Figure 12:
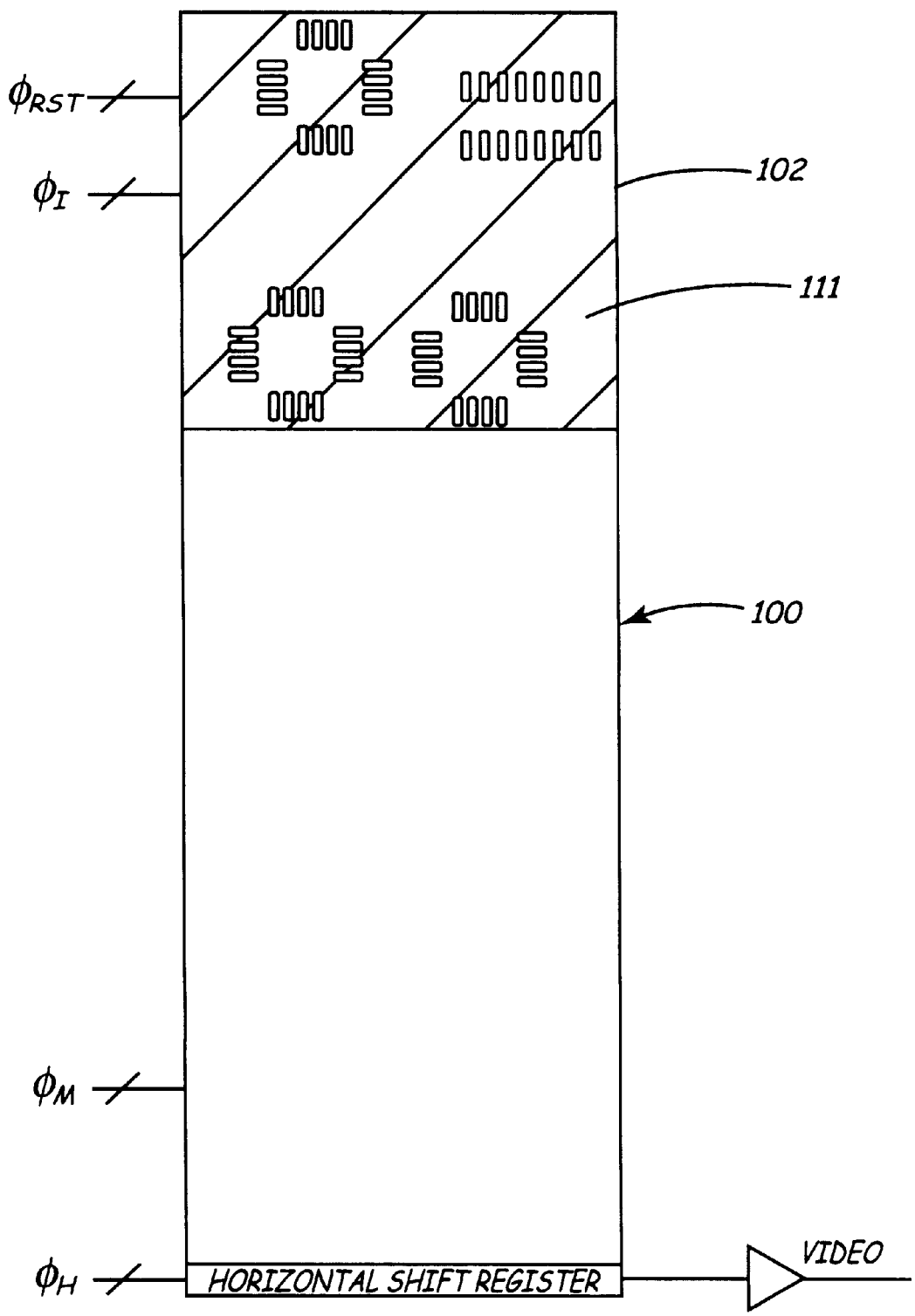
FIGS. 12–16 illustrate the status of a frame transfer CCD array at various stages during execution of the method shown in FIG. 11.
Figure 13:
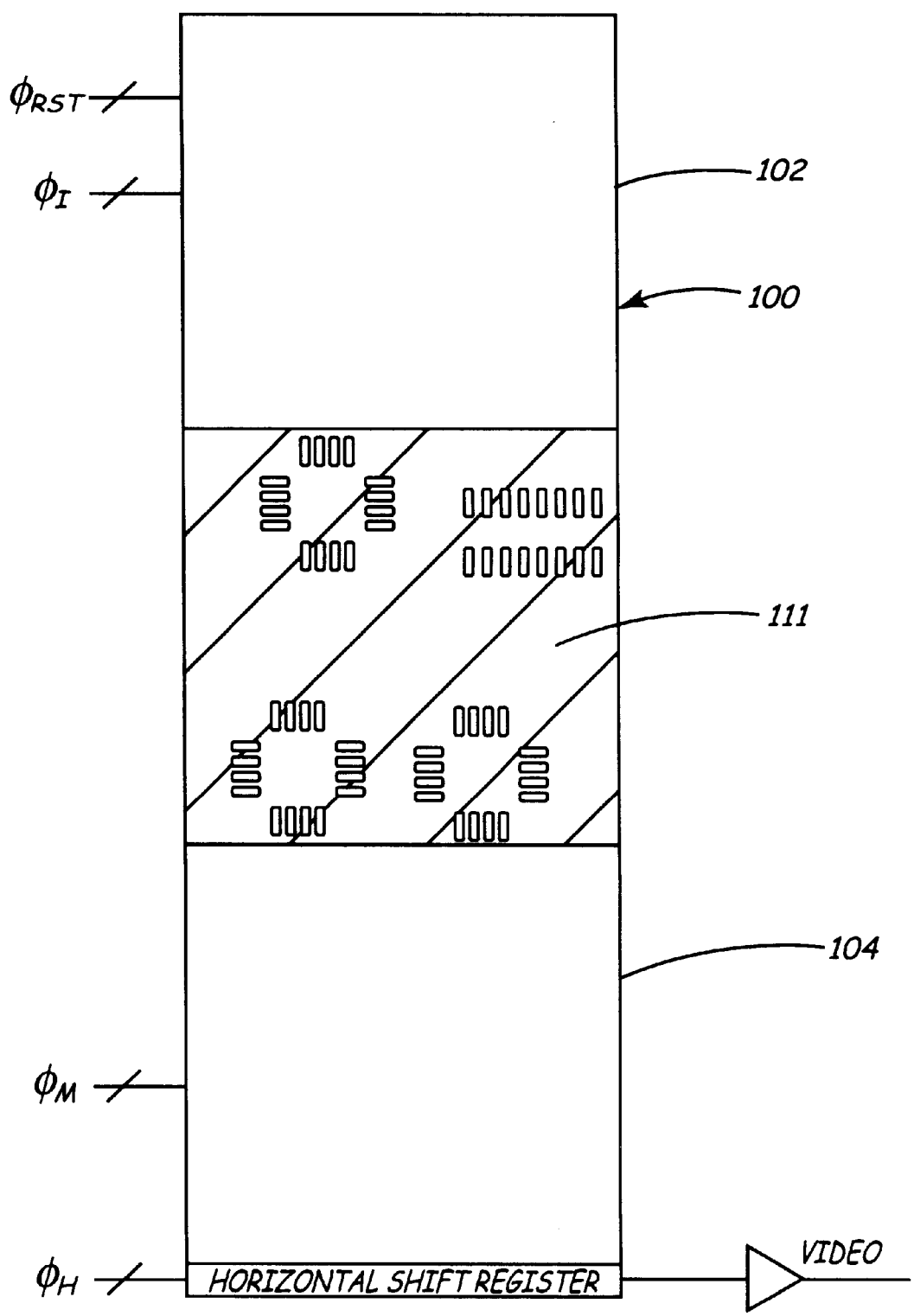
Figure 14:
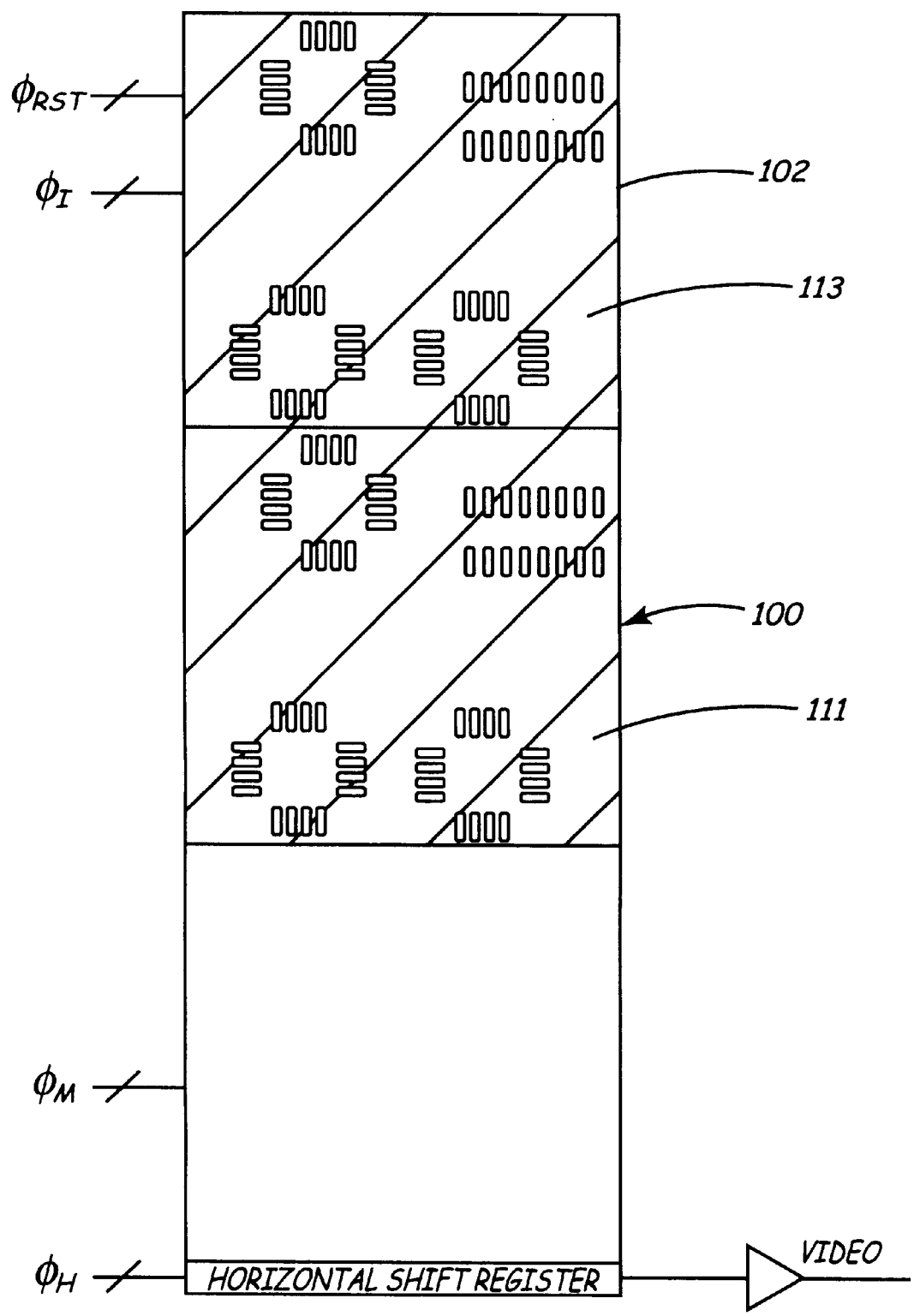
Figure 15:
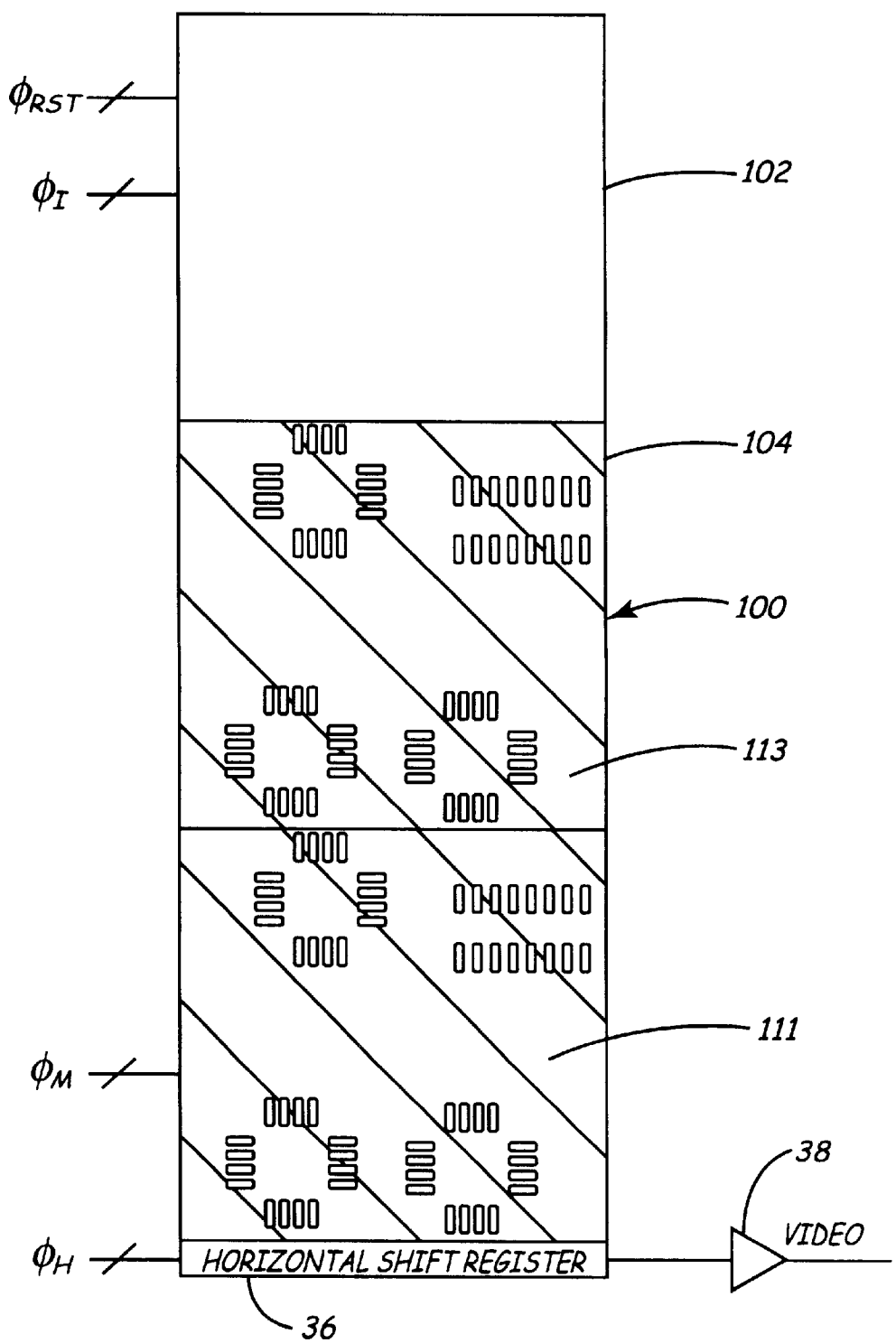
Figure 16:
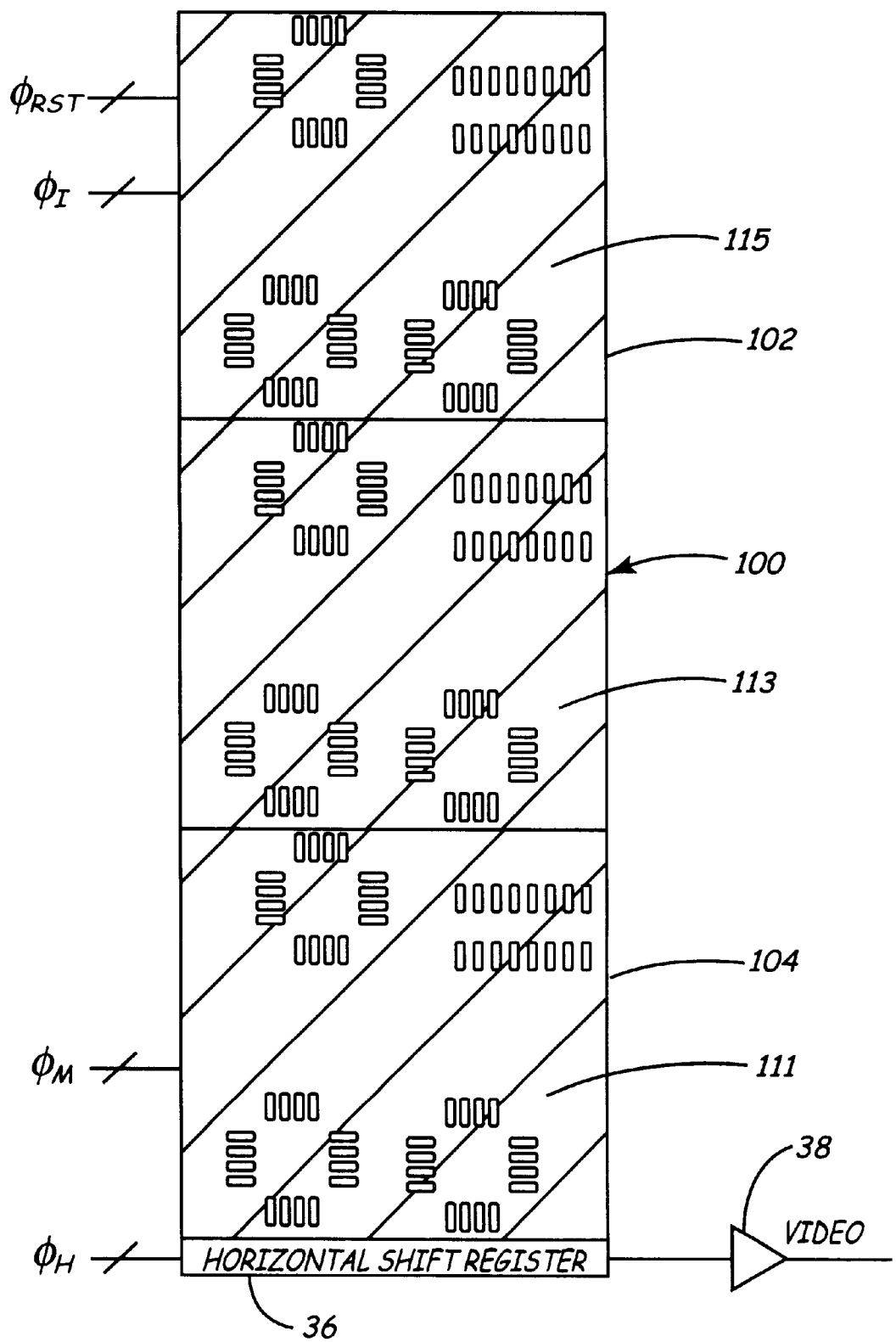

FIG. 11 is a method of quickly acquiring three or more fringe pattern images. The method begins at block 108 where image area 102 of CCD array 100 is reset using signal $\phi_{RST}$. At block 110, an illuminator is flashed to expose image area 102 to the first fringe pattern image. The results of block 110 are illustrated in FIG. 12 where first image 111 is shown stored in image area 102 of CCD array 100. Referring now to FIG. 11, after image 111 is acquired, control passes to block 112 where a high speed image transfer is effected by clocking $\phi_I$ and $\phi_M$ together 1,024 times to transfer image 111 of the first fringe pattern to the top half of the memory area 104. This transfer takes approximately 800 microseconds in the preferred embodiment. The results of block 112 are illustrated in FIG. 13. Once image 111 has been transferred to the top half of memory area 104, control passes to block 114 where image area 102 is exposed to another fringe pattern image. Preferably, in block 114, before image area 102 is exposed, a reset is performed in order to place image area 102 in the exact condition that it was in before acquiring image 111. Block 114 takes approximately 20 microseconds in this embodiment. The results of block 114 are illustrated in FIG. 14 where second fringe pattern image 113 is stored in image area 102 of CCD array 100. Once second image 113 has been acquired, control passes to block 116 where a high speed image transfer is performed by clocking $\phi_I$ and $\phi_M$ together 1,024 times to transfer second fringe pattern image 113 to the top half of memory area 104, as well as transfer first fringe pattern image 111 to the bottom half of memory area 104. The high-speed transfer of block 116 takes approximately 800 microseconds in this embodiment. The results of block 116 are illustrated in FIG. 15, which shows the first and second fringe pattern images 111, 113 stored in the memory area 104 of CCD array 100. Once block 116 has executed, control passes to block 118 where an image area reset is preferably performed before image area 102 is again exposed in order to acquire third fringe pattern image 115. Block 118 preferably takes 20 microseconds for execution and results in image storage as illustrated in FIG. 16. At block 120, images 111, 113, and 115 are read down a line at a time, and read from shift register 106 until all three images have been read out. At block 121, the three images are used to compute a height map of the features.

A summary of the execution times for various steps of the method shown in FIG. 11 is set forth below in Table 2.

TABLE 2

| Function | Time |
|---|---|
| Flash and Acquire Image #111 | 20 microseconds |
| High Speed Transfer | 800 microseconds |
| Flash and Acquire Image #113 | 20 microseconds |
| High Speed Transfer | 800 microseconds |
| Flash and Acquire Image #115 | 20 microseconds |
| Total | About 1.7 milliseconds |

| Function | Time |
|---|---|
| Flash and Acquire Image 131 | 20 microseconds |
| Transfer H/2 | 400 microseconds |
| Flash and Acquire Image 133 | 20 microseconds |
| Transfer H/2 | 400 microseconds |
| Flash and Acquire Image 133 | 20 microseconds |
| Total | About 1 milliseconds |

The total image acquisition time shown in Table 2 represents a significant improvement, and is relatively close to the stated goal of one millisecond and is sufficient for environments of mild vibration.

Figure 17:
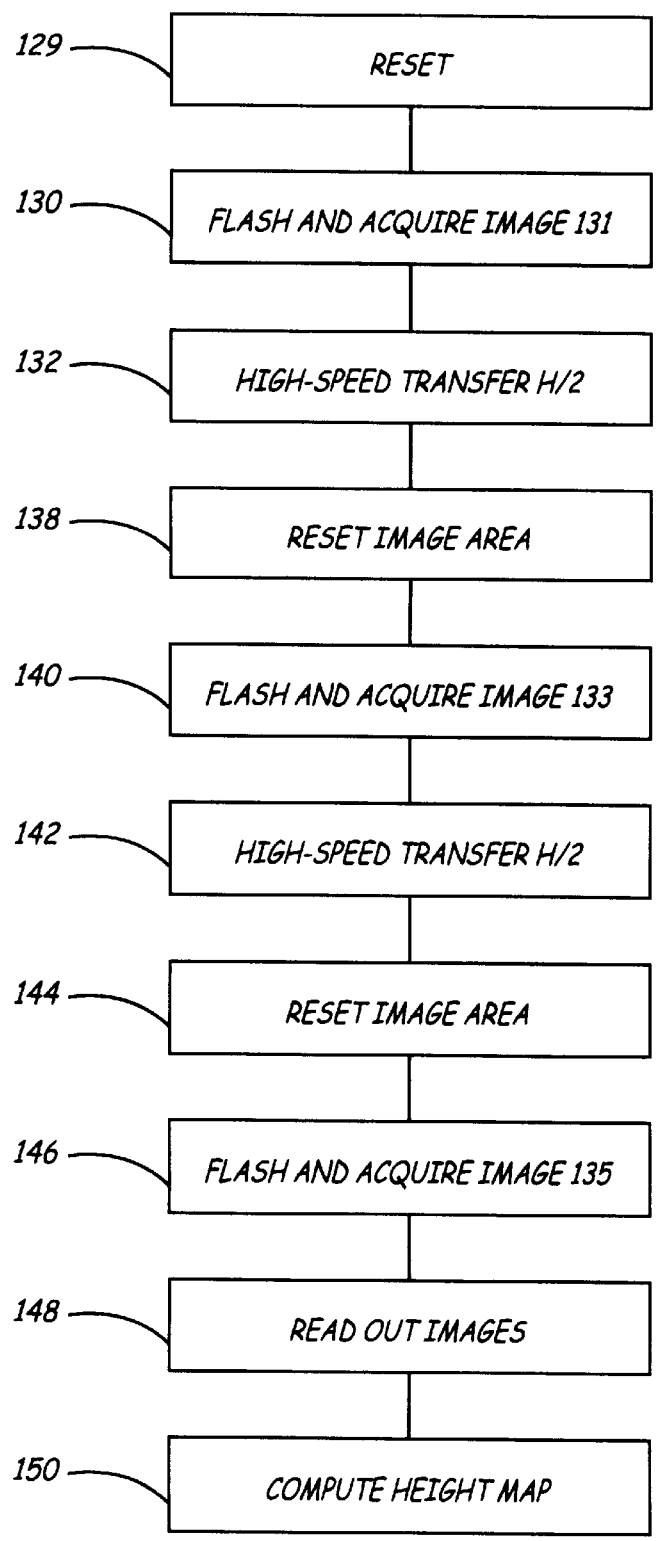
FIG. 17 is a block diagram of a method of acquiring three fringe pattern images with a conventional frame transfer CCD array.
Figure 18:
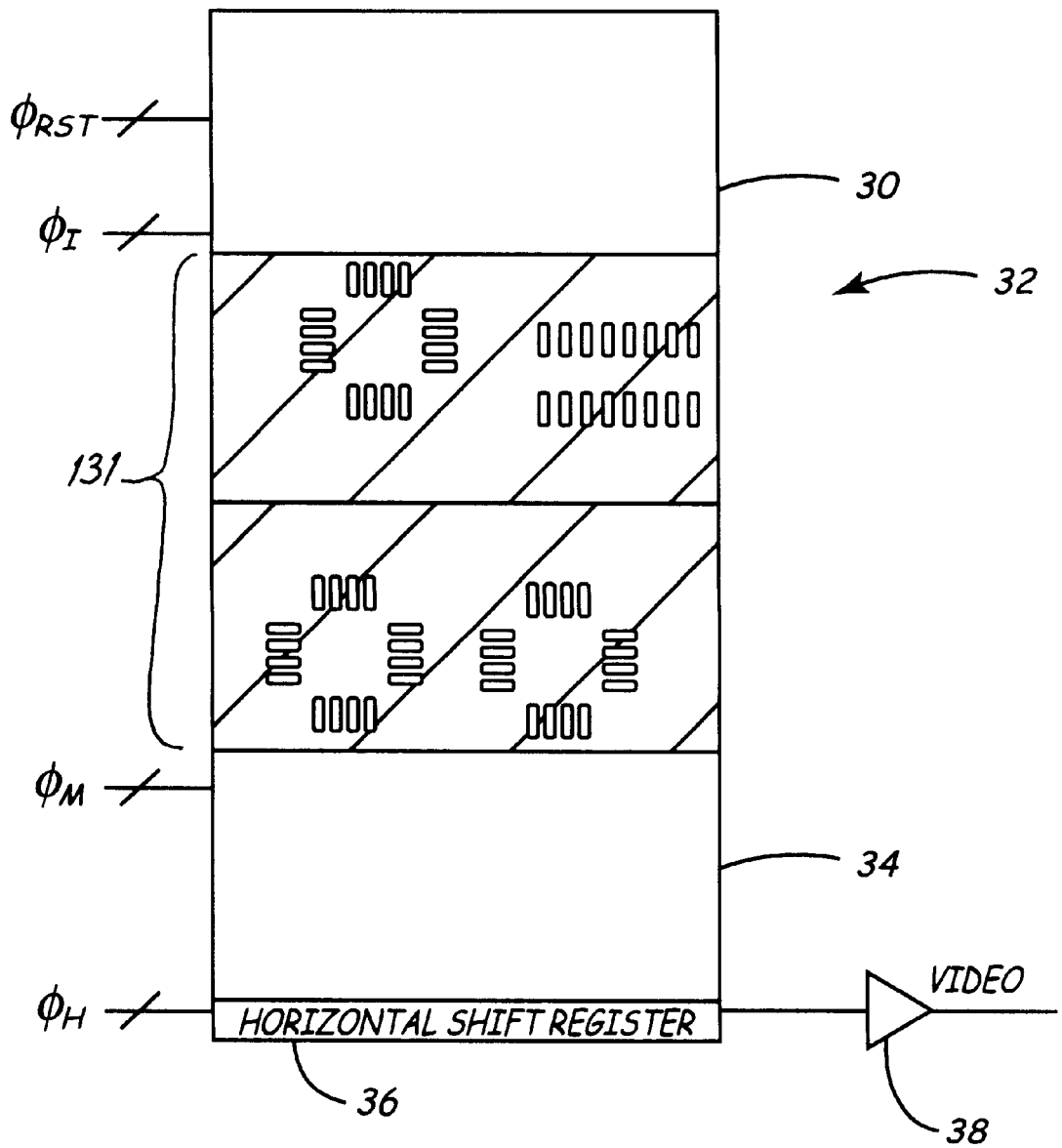
FIGS. 18–23 illustrate the status of a frame transfer CCD array at various stages during the method shown in FIG. 17.
Figure 19:
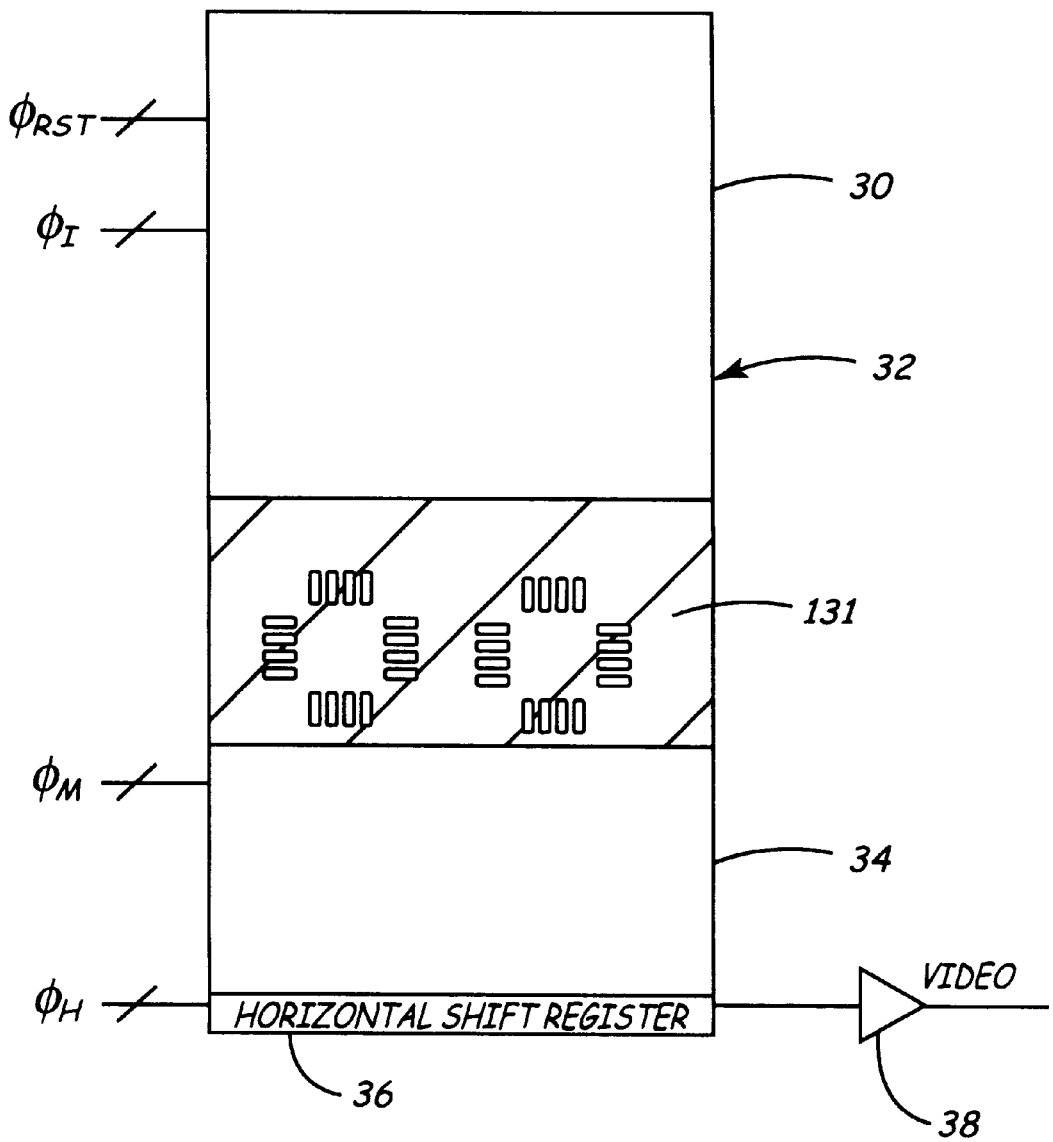
Figure 20:
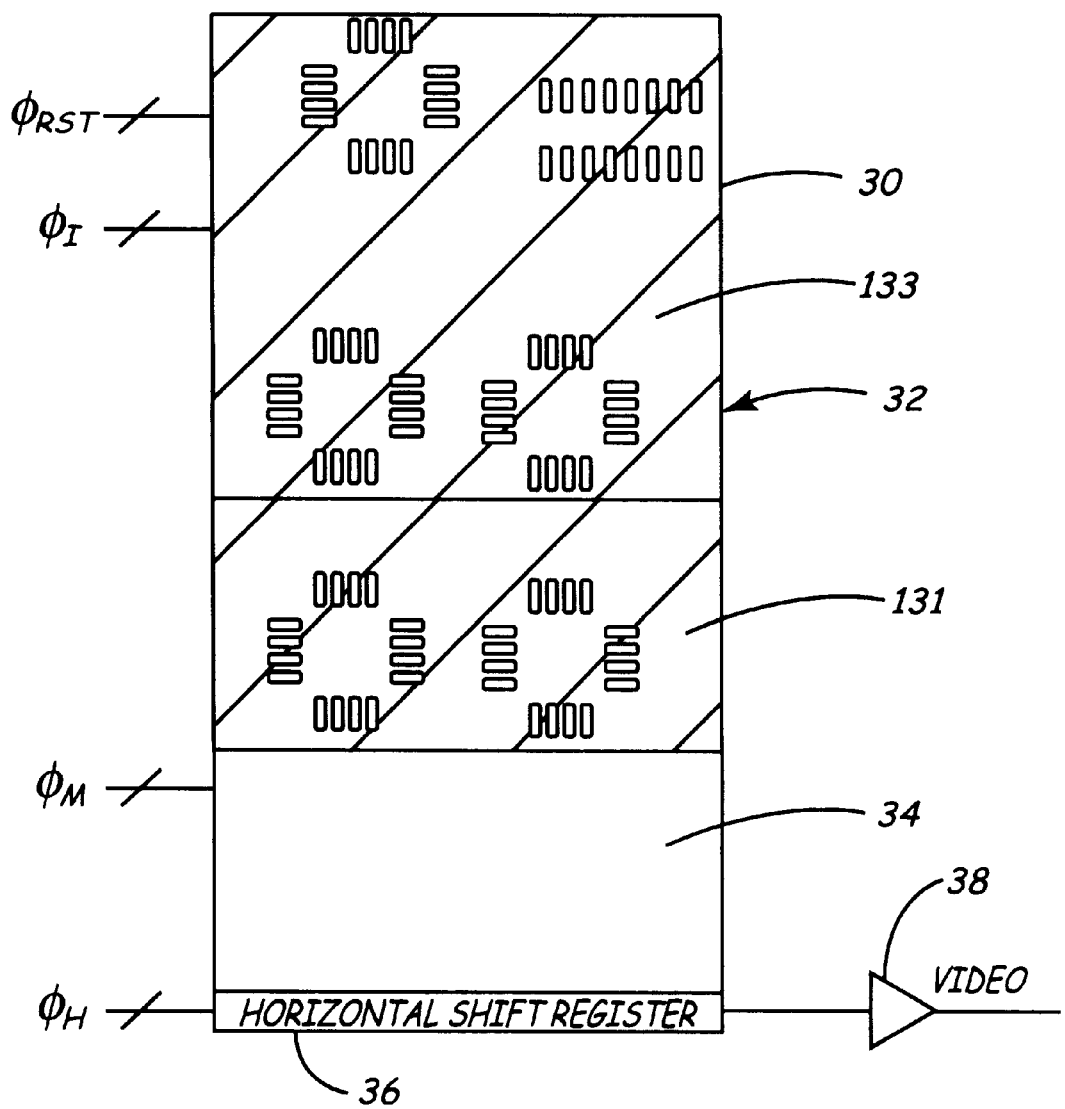
Figure 21:
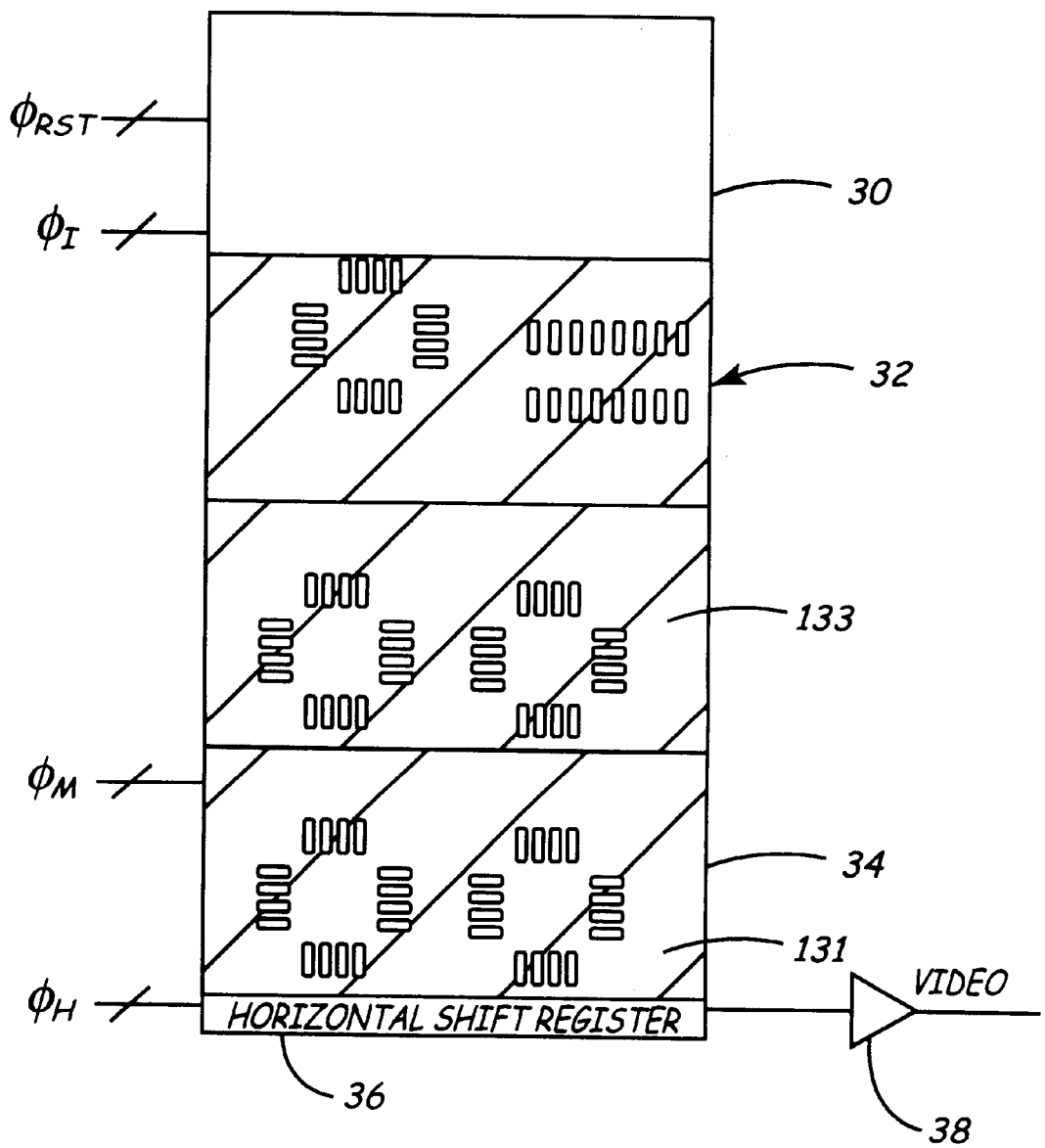
Figure 22:
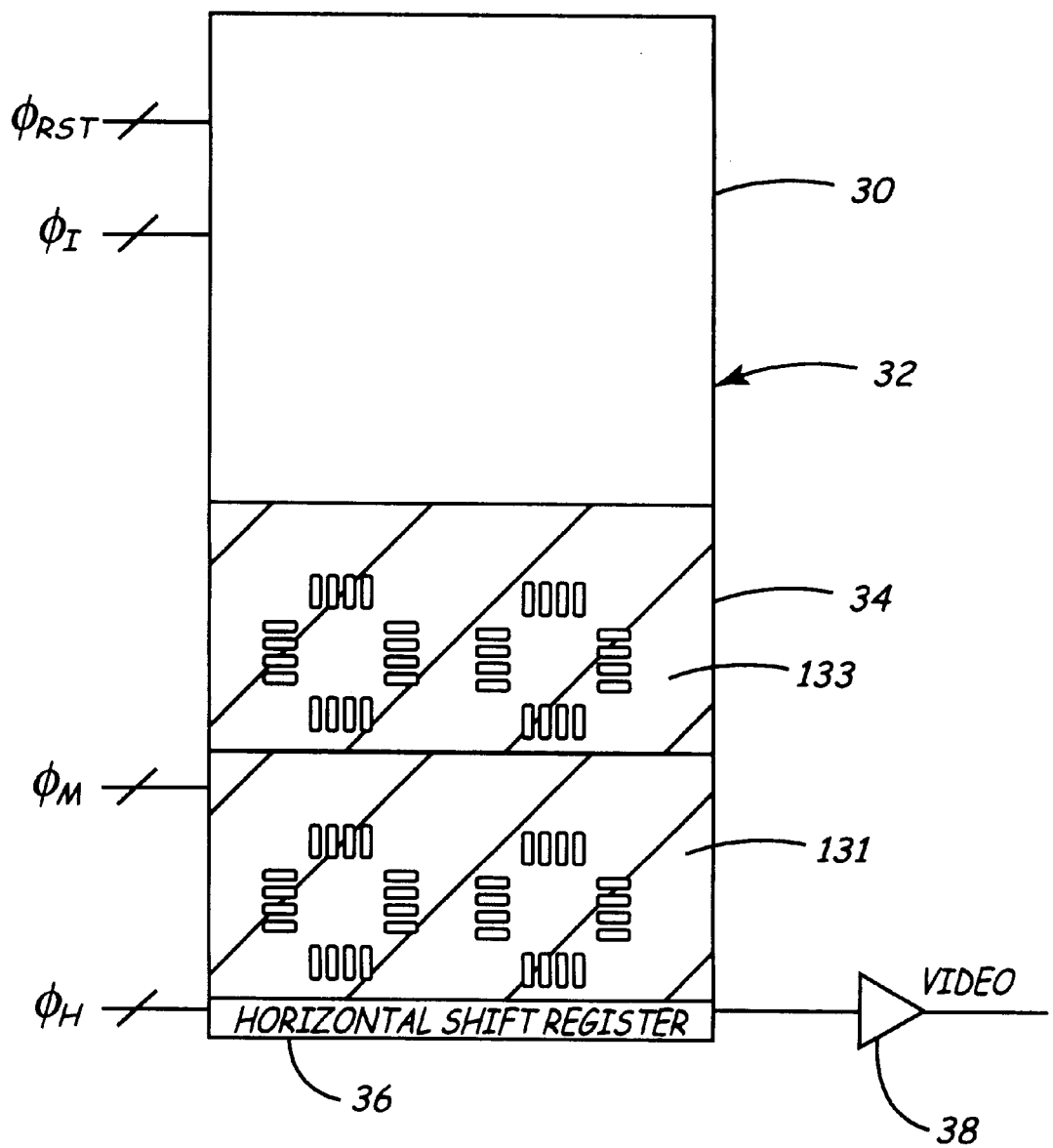
Figure 23:
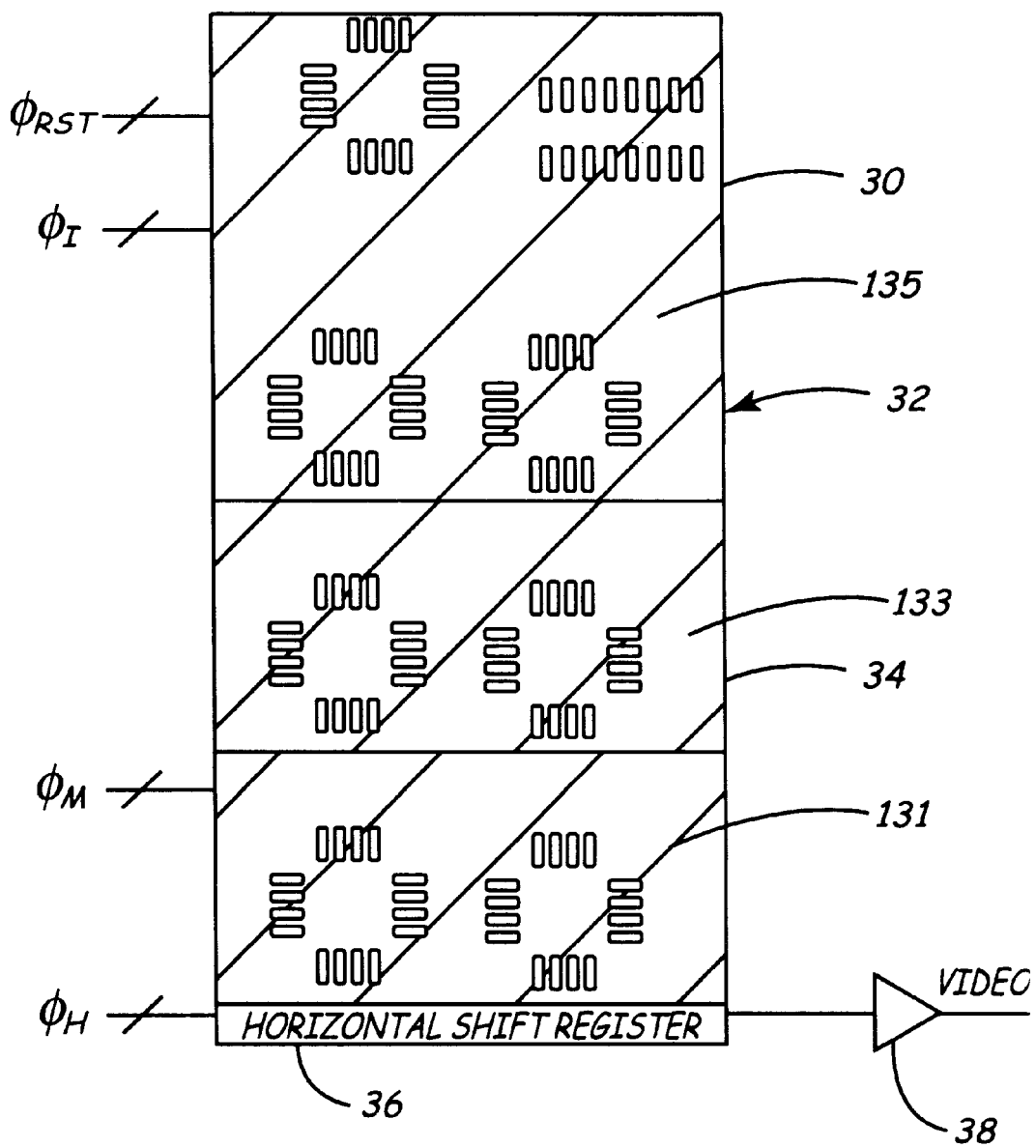

A method of quickly capturing three fringe pattern images onto a commercially available frame transfer CCD array (shown in FIG. 3) is illustrated in FIG. 17. The method begins at block 129 where image area 30 is reset. At block 130, an illuminator is flashed to expose image area 30 of conventional CCD array 32 to first fringe pattern image 131. This step generally takes approximately 20 microseconds. Once first fringe pattern image 131 has been acquired, control passes to block 132 where a high speed image transfer is performed by clocking $\phi_I$ and $\phi_M$ together 512 times, to shift first fringe pattern image 131 downward into memory area 34 of frame transfer CCD array 32 a length of H/2. The results of block 132 are shown in FIG. 18 where the bottom half of first fringe pattern image 131 has been transferred to the top half of memory area 34. This transfer takes approximately 400 microseconds. Referring back to FIG. 17, after the completion of the high speed transfer described in block 132, control passes to block 138 where image area 30 is reset. This is performed by clocking the reset clock line, $\phi_{RST}$, which clears all the data in images area 30, but not in memory space 34. Once the image area has been reset in block 138, only a portion of first fringe pattern image 131 will exist in the top half of the memory area. This stage is illustrated in FIG. 19. In effect, the top half of the first fringe pattern image has been erased. The reset step takes approximately 2 microseconds. Referring back to FIG. 17, after the reset has been completed, control passes to block 140 where the illuminator is flashed again to expose the image area to second fringe pattern image 133. This image acquisition takes approximately 20 microseconds. The results of block 140 are illustrated in FIG. 20. Once second fringe pattern image 133 has been acquired, another high speed transfer is accomplished by clocking $\phi_I$ and $\phi_M$ together to shift the second fringe pattern image downward by half its length, H/2, indicated at block 142. At this point, the bottom half of the first fringe pattern is in the bottom of memory area 34 and the bottom half of second fringe pattern 133 is in the top half of memory area 34. This transfer takes approximately 400 microseconds and the results are shown in FIG. 21. Once the high speed transfer of block 142 is complete, image area 30 of frame transfer CCD array 32 is reset by clocking the $\phi_{RST}$, which essentially erases the top half of the second fringe pattern image. The results of the second reset are illustrated in FIG. 22. Once block 144 has finished, control passes to block 146 where the image area 30 is exposed to third fringe pattern image 135. This takes approximately 100 microseconds and the results are shown in FIG. 23. At block 148, all three images are read from CCD array 32. A height map of the imaged features is computed at block 150 based upon images 131, 133, and 135.

Sample times for various steps are shown in Table 3 below.

After the method illustrated in FIG. 17 has executed, three fringe pattern images of size W by H/2 will have been captured within the time span of approximately 1 millisecond using a conventional frame transfer CCD array. The final three fringe pattern images will have sizes of 1,024 pixels in width and 512 pixels in height. This meets the temporal goal that provides the vibration immunity listed above. The fringe pattern images are then read out by shifting down the image and memory areas a line at a time and clocking the charge packets out of the horizontal shift register until all three fringe pattern images of size W by H/2 have been read out.

In order for the method of the present invention to execute properly, frame transfer CCD array 32 should be capable of resetting image area 30 without disrupting data previously moved into the storage or memory 34 (an asynchronous reset of image space 30). Thus, after the image area has been exposed to the first and second fringe pattern images, these images are both in memory area 34. The image should be cleared of the top half of the first and second fringe pattern images before subsequent exposures occur. Without the ability to asynchronously reset the image area, the only method to clear the image area is to completely shift the whole image area into the memory area. This would have the adverse effect of "pushing" the first fringe pattern image out of the memory area.

Although the present invention has been described with reference to preferred embodiments, workers skilled in the art will recognize that changes may be made in form and detail without departing from the spirit and scope of the invention. For example, although the method of the present invention has been described in relation to acquiring three images, it is extendable to rapidly capture more than three images with a commercially available frame transfer CCD array. For example, to capture four images in rapid succession, the high speed image transfer step would only shift the first three images down by H/3 before the image area reset operation. This would result in rapidly capturing four images of size W by H/3.

Furthermore, it is understood by workers skilled in the art that the invention is not limited to use of the specific signals to accomplish certain described functions. For example, other CCD frame transfer arrays which operate on substantially the same principles as those disclosed herein are equally applicable for the present invention. Finally, the method and apparatus of the present invention are usable for any purpose which requires acquisition of multiple images within a limited time period, such as, for example, high speed photography of objects moving at a high velocity.

What is claimed is:

1. A method of acquiring at least two images with a single frame transfer CCD array, the method comprising:

a) illuminating an object, and acquiring a first image on an image area of the array;

b) shifting at least a portion of the first image into a memory area of the array;

c) resetting the image area of the array; and d) illuminating the object and acquiring a second image on the image area of the array, while the first image is in the memory area of the single frame transfer CCD array; and wherein the at least two images are acquired within about 1 millisecond.

2. The method of claim 1, wherein object height is computed based upon the at least two images.

3. A solder paste inspection system performing the method of claim 2.

4. A solder paste inspection system performing the method of claim 1.

5. The method of claim 1, wherein the illumination is in the visible spectrum.

6. A method of acquiring at least three fringe pattern images on a surface feature, the method comprising:

successively acquiring at least first, second, and third fringe pattern images with a single frame transfer CCD array;

wherein all images are acquired before any data is read from the CCD array; and wherein all images are acquired within about 1 millisecond.

7. A method of acquiring three fringe pattern images of a feature with a single frame transfer CCD array having an image area with a width W and a height H, and a memory area, the method comprising:

a) exposing the feature with a first fringe pattern, and acquiring a first image thereof on the image area;

b) shifting the first image by a distance corresponding to a length of H/2;

c) resetting the image area of the array;

d) exposing the feature with a second fringe pattern, and acquiring a second image thereof on the image area;

e) shifting the second image by a distance corresponding to a length of H/2;

f) resetting the image area of the array;

g) exposing the feature with a third fringe pattern, and acquiring a third image thereof on the image area; and h) shifting the first, second and third images out of the array.

8. The method of claim 7, wherein the first second, and third images each have a size substantially of W by H/2.

9. The method of claim 7, wherein the steps of a) through h) are performed within a time period of about 2 milliseconds.

10. The method of claim 9, wherein the steps of a) through h) are performed within about 1 millisecond.

11. The method of claim 7, wherein feature height is computed based upon the first, second and third images.

12. A solder paste inspection system performing the method of claim 7.

13. The method of claim 7 wherein the memory area and the image area are of substantially the same size.

14. A method of capturing at least three video images on a surface feature with a single frame transfer CCD array having an image area and a memory area, the method comprising:

a) energizing an illumination source to project illumination on the surface feature;

b) acquiring an image in the image area;

c) transferring contents of the image area and the memory area by an amount equal to a fraction of the height of the image area;

d) resetting the image area of the CCD array;

e) repeating steps a) through c) a number of times equal to the inverse of the fraction and executing step d) between each iteration of steps a) through c); and wherein the inverse of the fraction is an integer greater than one.

15. The method of claim 14 wherein the memory area and the image area are of substantially the same size.

16. A method of acquiring three fringe pattern images of a feature with a single frame transfer CCD array having an image area with a width W and a height H and a memory area having a width W and a height 2H, the method comprising:

a) exposing the feature with a first fringe pattern of light, and acquiring a first image thereof on the image area;

b) shifting the first image completely into the memory area;

c) exposing the feature with a second fringe pattern of light, and acquiring a second image thereof on the image area;

d) shifting the second image completely into the memory area, e) exposing the feature with a third fringe pattern of light, and acquiring a third image thereof on the image area; and f) shifting the first, second and third images out of the array.

* * * * *